US011583670B2

(12) United States Patent
Pfeifer et al.

(10) Patent No.: US 11,583,670 B2
(45) Date of Patent: Feb. 21, 2023

(54) CATHETER FOR THE DIRECTIONAL CONVEYANCE OF A FLUID, PARTICULARLY A BODY FLUID

(71) Applicant: NovaPump GmbH, Jena (DE)

(72) Inventors: Joerg Pfeifer, Jena (DE); Patrick Patzer, Harth-Poellnitz (DE); Ronald Reich, Jena (DE)

(73) Assignee: NovaPump GmbH, Jena (DE)

( * ) Notice: Subject to any disclaimer, the term of this patent is extended or adjusted under 35 U.S.C. 154(b) by 578 days.

(21) Appl. No.: 16/723,534

(22) Filed: Dec. 20, 2019

(65) Prior Publication Data

US 2020/0121838 A1  Apr. 23, 2020

Related U.S. Application Data

(63) Continuation-in-part of application No. 15/449,744, filed on Mar. 3, 2017, now Pat. No. 10,512,714, and
(Continued)

(30) Foreign Application Priority Data

Mar. 3, 2014 (DE) ..................... 10 2014 003 153.5
Sep. 3, 2014 (DE) ..................... 10 2014 012 850.4

(51) Int. Cl.
*A61M 60/13* (2021.01)
*A61M 60/148* (2021.01)
(Continued)

(52) U.S. Cl.
CPC .......... *A61M 60/148* (2021.01); *A61M 60/13* (2021.01); *A61M 60/139* (2021.01);
(Continued)

(58) Field of Classification Search
CPC .. A61M 60/13; A61M 60/139; A61M 60/148; A61M 60/295; A61M 60/427;
(Continued)

(56) References Cited

U.S. PATENT DOCUMENTS 4,931,036 A * 6/1990 Kanai ................. A61M 60/295
604/920
5,460,607 A * 10/1995 Miyata ............... A61M 60/295
604/99.04
(Continued)

FOREIGN PATENT DOCUMENTS

DE         35 25 1 65 A1   1/1987
DE    10 2004 002 843 A1   8/2005
(Continued)

OTHER PUBLICATIONS

International Search Report dated Jun. 26, 2015 of international application PCT/DE2015/100081 on which this application is based.
(Continued)

*Primary Examiner* — Benjamin J Klein
(74) *Attorney, Agent, or Firm* — Walter Ottesen, P.A.

(57) ABSTRACT

A catheter directionally conducts a pulsating body fluid and has a line segment defining an inner volume. A pump chamber section is arranged proximally as an extension of the line segment and defines a pump chamber having a frame therein accommodating a balloon. A first opening connects the inner volume to an external volume and a second opening is arranged proximally from the first opening to connect the inner volume to the external volume. A check valve is assigned to the second opening and the check valve includes a valve foil having an aperture formed therein offset from the second opening. A third opening communicates with the pump chamber. The frame is of a shape memory material which provides rigidity for a pulsatile operation of the balloon. During operation, the pulsating body fluid is
(Continued)

conveyed in the inner volume directionally between the first and second opening by operating the balloon.

24 Claims, 15 Drawing Sheets

Related U.S. Application Data a continuation-in-part of application No. 15/257,647, filed on Sep. 6, 2016, now abandoned, and a continuation of application No. PCT/DE2015/100369, filed on Sep. 2, 2015, and a continuation of application No. PCT/DE2015/100081, filed on Mar. 2, 2015.

(51) Int. Cl.
*A61M 60/43* (2021.01)
*A61M 60/562* (2021.01)
*A61M 60/896* (2021.01)
*A61M 60/427* (2021.01)
*A61M 60/497* (2021.01)
*A61M 60/295* (2021.01)
*A61M 60/865* (2021.01)
*A61M 60/139* (2021.01)

(52) U.S. Cl.
CPC ........ *A61M 60/295* (2021.01); *A61M 60/427* (2021.01); *A61M 60/43* (2021.01); *A61M 60/497* (2021.01); *A61M 60/562* (2021.01); *A61M 60/865* (2021.01); *A61M 60/896* (2021.01); *A61M 2205/0216* (2013.01); *A61M 2205/0266* (2013.01); *A61M 2205/05* (2013.01)

(58) Field of Classification Search
CPC .. A61M 60/43; A61M 60/562; A61M 60/865; A61M 60/896; A61M 2205/0216; A61M 2205/0266; A61M 2205/05
See application file for complete search history.

(56) References Cited

U.S. PATENT DOCUMENTS

| | | | |
|---|---|---|---|
| 5,928,132 | A | 7/1999 | Leschinsky |
| 6,544,216 | B1* | 4/2003 | Sammler ............. A61M 60/237 604/95.03 |
| 7,070,555 | B2 | 7/2006 | Siess |
| 8,409,128 | B2* | 4/2013 | Ferrari ................ A61M 1/3667 604/9 |
| 8,932,246 | B2 | 1/2015 | Ferrari |
| 2003/0144573 | A1* | 7/2003 | Heilman ................. F16K 15/18 600/16 |
| 2007/0197855 | A1 | 8/2007 | Richardson et al. |
| 2009/0270815 | A1 | 10/2009 | Stamp et al. |
| 2010/0268017 | A1* | 10/2010 | Siess ................... A61M 60/237 600/16 |
| 2012/0234411 | A1* | 9/2012 | Scheckel ............. A61M 60/808 137/565.01 |
| 2014/0288354 | A1 | 9/2014 | Timms et al. |
| 2019/0117865 | A1* | 4/2019 | Walters ............... A61M 60/531 |
| 2020/0376179 | A1* | 12/2020 | Patzer ................... A61M 60/13 |

FOREIGN PATENT DOCUMENTS

| | | | |
|---|---|---|---|
| DE | 102014003153 | A1 | 9/2015 |
| EP | 0 608 846 | A2 | 8/1994 |
| GB | 1 370 546 | A | 10/1974 |
| WO | 97/02850 | A1 | 1/1997 |
| WO | WO-2019071148 | A1 * | 4/2019 ....... A61B 17/12109 |

OTHER PUBLICATIONS

International Search Report dated Mar. 11, 2016 of international application PCT/DE2015/100369 on which this application is based.

\* cited by examiner

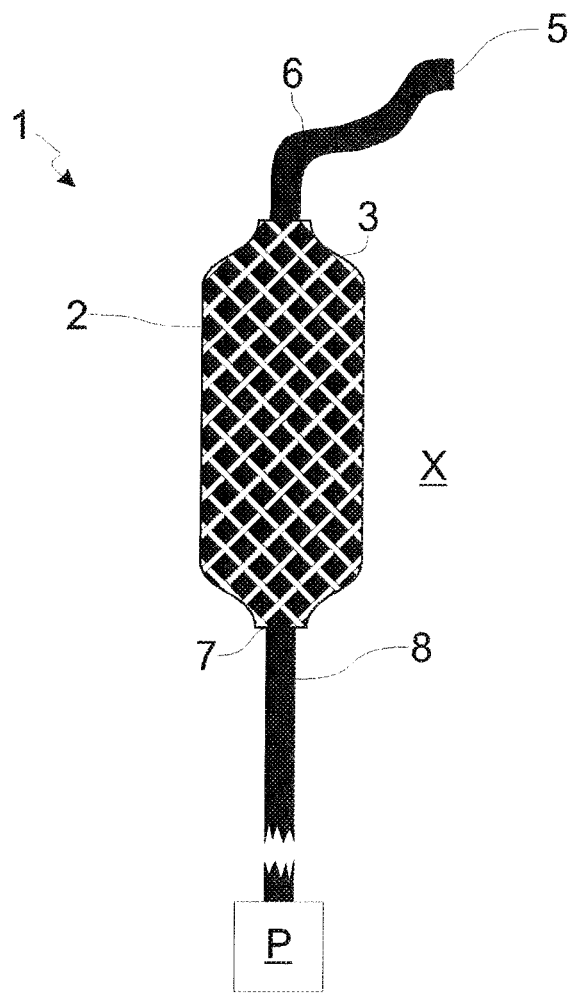
Fig. 1 - Prior Art

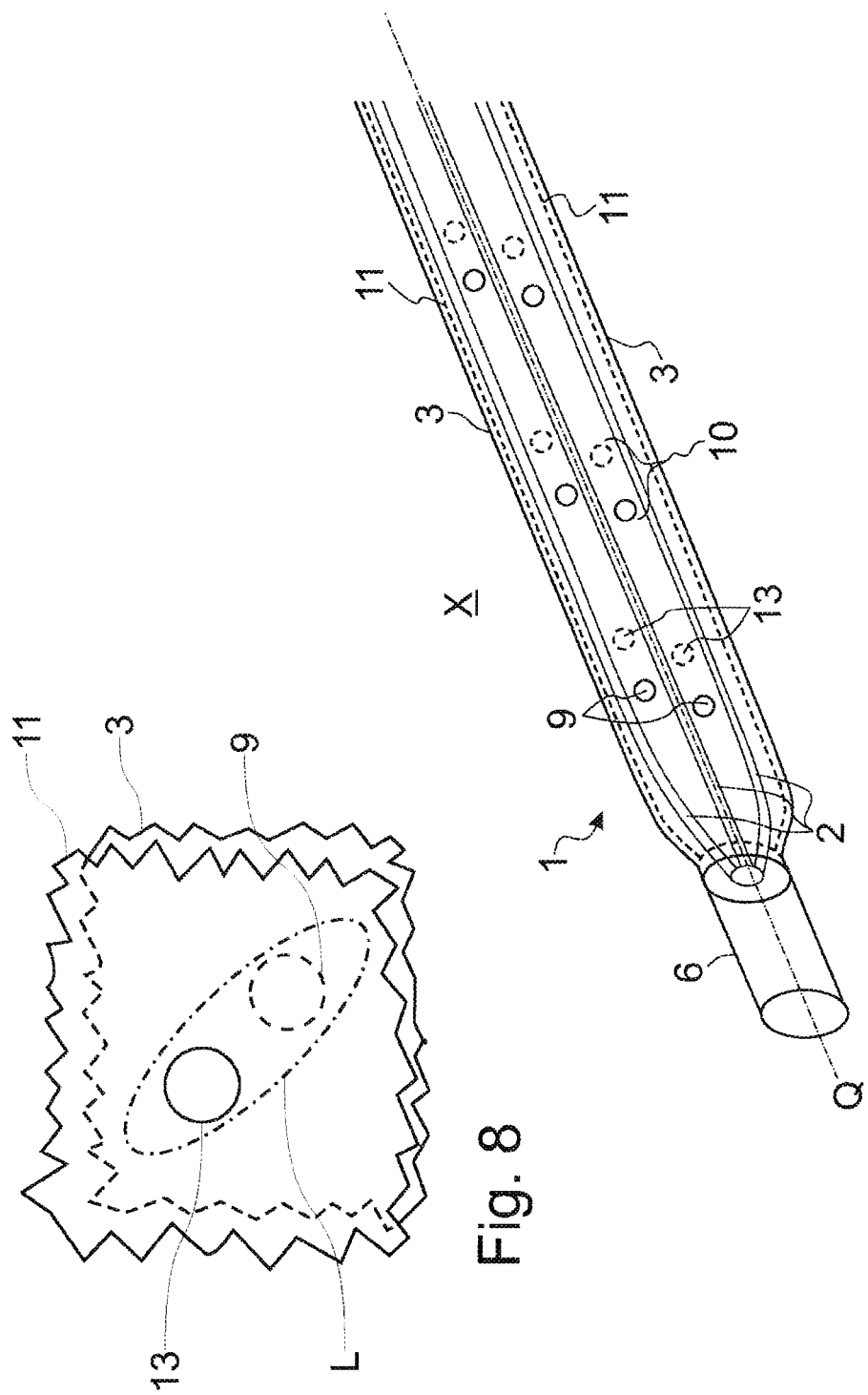

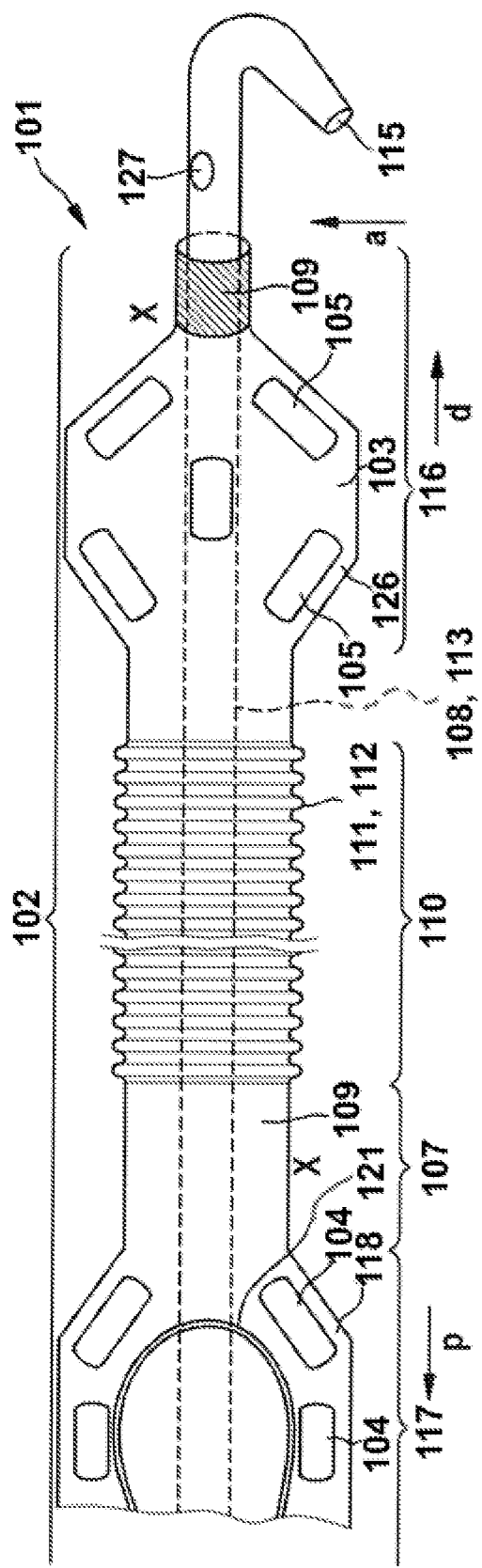
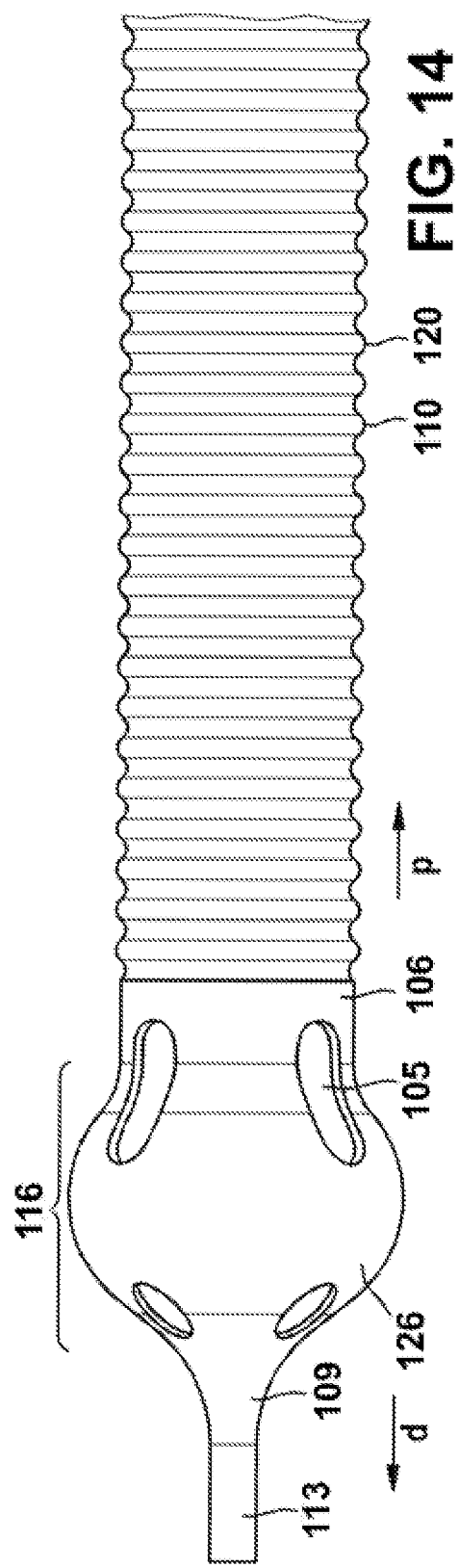

CATHETER FOR THE DIRECTIONAL CONVEYANCE OF A FLUID, PARTICULARLY A BODY FLUID

CROSS REFERENCE TO RELATED APPLICATIONS

This application is a continuation-in-part application of U.S. patent application Ser. No. 15/257,647 filed on Sep. 6, 2016, which, in turn, is a continuation application of international patent application PCT/DE2015/100081, filed Mar. 2, 2015, designating the United States and claiming priority from German application 10 2014 003 153.5, filed Mar. 3, 2014. Also, this application is a continuation-in-part application of U.S. patent application Ser. No. 15/449,744, filed on Mar. 3, 2017, which, in turn, is a continuation application of international patent application PCT/DE2015/100369, filed Sep. 2, 2015, designating the United States and claiming priority from German application 10 2014 012 850.4, filed Sep. 3, 2014, the entire contents of the above applications are incorporated herein by reference.

FIELD OF THE INVENTION

The invention relates to a catheter for the directional conveyance of a (bodily) fluid, in particular a body fluid. The catheter includes a sleeve having an internal space and a frame, wherein the sleeve has at least three openings (and is fluid-tight with respect to the fluid being conveyed aside from these openings), and is configured at least in a region between the first opening and the second opening as a line for the fluid. A check valve is arranged at the second opening to make possible an exclusively unidirectional flow between the internal volume of the sleeve and the external space surrounding the sleeve.

"Distal" in the context of the invention means "toward the end of the catheter which has been inserted into the body". Accordingly, in the catheter according to the invention a second port arranged distally from a first port is arranged closer to the distal end of the catheter (that is, the catheter end which has been pushed into the body as intended) than the first port. "Proximal" in the context of the invention means "away from the distal catheter end". Accordingly, in the catheter according to the invention, a proximal end of the catheter is arranged opposite the distal catheter end, and typically protrudes out of the body when the catheter has been inserted into the body as intended.

BACKGROUND OF THE INVENTION

In the context of the invention, the expression "fluid-tight" means an impermeability to atoms or molecules of the fluid in question, under the maximum conditions prevailing in this fluid in the living human body. If the catheter is, for example, configured for conveying blood, then "fluid-tight" means an impermeability at least up to a maximum human blood pressure.

A catheter of the type named above, having multiple check valves, is known in the prior art, for example from U.S. Pat. Nos. 8,932,246 and 8,409,128. The catheter is preferably used in cases of limited cardiac output to support the heart and the blood circulation. The catheter can also be used in cases of more advanced aortic regurgitation. The catheter serves the purpose of transporting the conveyed fluid from a first location to another location without significantly increasing the pressure of the fluid at the first location beyond a state determined by physiology by implementing the principle of a submersible pump and by combining it with the principle of a diaphragm pump due to the use of a balloon catheter. The direction of conveyance (flow direction) depends in this case on the orientation of the check valves. It thus enables, compared to the known intra-aortic balloon pump counterpulsation, a directional transport of the body fluid with less stress on the patient.

Such catheters can be called pump catheters for short. However, it is possible to use a separate drive, especially in the form of an adjustable displacement device, for example a balloon catheter of an intra-aortic balloon pump (IABP). The catheter is, in its basic form, simply a non-driven line catheter. The pump catheter can be implemented by pushing the displacement device following the placement of the catheter line, through the third opening into the internal space of the sleeve.

Therefore, it is possible and practical to implement the line catheter without a drive.

The complexity involved, and the negative impacts on the patient, in a minimally invasive insertion of a catheter into the body, for example via inguinal vessels, essentially depend on the size—and particularly the largest outer diameter—of the catheter.

A catheter of the type mentioned is known in the prior art from, by way of example, U.S. Pat. Nos. 8,932,246 and 8,409,128. It is preferably used in cases of limited cardiac output to support the heart and the blood circulation. In particular, it can also be used in cases of higher-grade aortic insufficiency. It is used to transport the conveyed body fluid from a first location to another location, without increasing the pressure of the fluid at the first location significantly above the physiologically specified state, by utilizing the principle of a submersible pump, and preferably by the use of a balloon catheter combined with the principle of a diaphragm pump, wherein the term 'submerged pump' is used to mean a pump which is immersed in the fluid being conveyed, and the term 'diaphragm pump' is used to mean a pump with a drive which is separated by a membrane from the fluid being conveyed. Thus it allows, compared to the known method of intra-aortic balloon counterpulsation, a directional transport of the body fluid, as well as less stress on the patient.

Such catheters can be referred to as pump catheters as well. It is possible to use a separate drive in such a pump catheter. The catheter is then, in its basic form, merely a drive-less line catheter. The pump catheter can then be created, for example, by inserting an adjustable displacement device—for example, a balloon catheter of an intra-aortic balloon pump (IABP)—into the internal volume of the catheter after the line catheter has been placed. As such, it is reasonably possible to furnish the catheter without a drive as well.

The complexity, and the stress on the patient, of a minimally invasive insertion of a catheter into the body—for example via groin vessels—substantially depends on the size, particularly the largest outer diameter, of the catheter. Therefore, from the perspective of the patient and the attending physician, it is best for the outer diameter of the catheter to be as small as possible. On the other hand, in order to ensure the required pump power—that is, the volume of fluid to be transported per unit of time—along with the lowest possible loads on the fluid being transported, the largest possible inner diameter—at least in the section of the catheter through which the fluid must be transported—is advantageous.

SUMMARY OF THE INVENTION

It is an object of the invention to provide a catheter of the type named above which has a smaller size.

The catheter of the invention is for the directional conduction of a pulsating body fluid including blood. The catheter includes: a line segment defining an inner volume and including a distal tube; a reinforcement running in the inner volume; a pump chamber section arranged proximally as an extension of the line segment; the pump chamber section defining a pump chamber having a frame disposed therein; a first opening connecting the inner volume to an external volume; a second opening arranged proximally from the first opening to connect the inner volume to the external volume; a check valve assigned to the second opening and the check valve including a valve foil having an aperture formed therein offset away from the second opening; a third opening communicating with the pump chamber; a balloon being arranged in the pump chamber and within the frame; the frame having a composition which comprises a shape memory material; the shape memory material providing sufficient rigidity for a pulsatile operation of the balloon disposed within the frame; a line for an auxiliary fluid for inflating the balloon being connected to the balloon; the line passing out through the third opening of the catheter and being connectable to a pump for the auxiliary fluid; and, wherein, during operation of the catheter, the pulsating body fluid is conveyed in the inner volume directionally between the first opening and the second opening by operating the balloon, such that, when deflating, drawing body fluid into the catheter and, when inflating, driving the drawn-in body fluid directionally through the line segment.

According to an aspect of the invention, the check valve includes a (flexible) valve foil which is at least partially attached to the sleeve in such a manner that the second opening can be (reversibly) completely covered by the valve foil. For the purposes of the invention, the valve foil is a sheet of any material with a maximum thickness of 0.2 mm. Reversible means that the second opening can be alternately opened and covered by the valve foil.

The valve foil thus forms, with the sleeve, a foil valve which only allows unidirectional flow of the fluid through the same. In the direction of passage, fluid pressing against the valve foil can lift the valve foil of the second opening and thereby flow past the foil valve. In the direction which is blocked, the fluid presses the valve foil against the second opening, which is then covered as a result. Then the fluid cannot pass through the foil valve. Compared to the prior art, which describes mechanically rigid and thus space-intensive check valves, the foil valve according to an aspect of the invention is only a negligible presence due to the minimal thickness of the valve foil, such that the catheter when folded can have a lower greatest external diameter (hereinafter also referred to as total diameter) than the prior art. This is advantageous in particular in the field of cardiology because experience has shown that, when the overall diameter of cardiac catheters is reduced, it is necessary to exclude fewer patients of a particular patient population from a surgical operation due to their specific inner blood vessel diameter. In addition, the safety of the implantation and explanation can be improved by decreasing the overall diameter.

If there is no pressure difference between the internal space and the external space, the valve foil can either lie against the sleeve (due to a mechanical preload and/or due to its geometrical profile), or the valve foil can lie loosely in a position relative to the sleeve which is defined exclusively by the attachment thereof to the sleeve.

In general, the sleeve, particularly in the region of a radially symmetric or rotationally symmetric shell surface, can be shaped in such a manner that the second opening has an edge which is non-planar. The edge can be curved, for example, in three dimensions in the case of a cylindrical surface. Only foil valves according to an aspect of the invention enable, with minimal structural complexity, a fluid-tight seal of openings with edges curved in three dimensions.

The valve foil can be attached directly or indirectly to the sleeve. In the case of a direct attachment, the valve foil can be glued, welded, or clamped to the sleeve, for example along a line of attachment. The attachment along the attachment line can be continuous or discontinuous, for example in a dotted line. In the case of an indirect attachment, the valve foil can be attached by way of example along the attachment line to an intermediate body, either by gluing, welding or clamping, wherein the intermediate body in turn can be attached, for example, along an auxiliary attachment line directly or indirectly to the sleeve and/or to another intermediate body. The intermediate body can, for example, be formed by the frame.

The attachment line can have any desired shape. For example, it can be straight within the plane of the valve foil. The attachment line can particularly form a substantially straight line or partially surround the second opening.

When there is a positive pressure difference in the blocking direction of the check valve, the valve foil lies substantially flat against the sleeve (that is, apart from wrinkles) and thereby covers the second opening in a fluid-tight manner. In contrast, when there is a negative pressure difference, the valve foil is pushed away from the sleeve in the areas outside of the attachment line in such a manner that fluid can pass through the check valve in the direction of passage.

The valve foil preferably has at least one aperture which is arranged outside of the second opening when the second opening is completely covered. The aperture is therefore offset with respect to the second opening in such a manner that the aperture and the second opening do not overlap when covered. The valve foil then lies, when there is a positive pressure difference in the blocking direction of the check valve, substantially (that is, apart from wrinkles) flat against the sleeve, and is substantially parallel to the surface thereof. In this way, it covers the second opening in a fluid-tight manner.

In particular, the attachment line can run in a way such that the second opening and the aperture are enclosed together by the line. The accordingly reduced mobility achieves a higher operational reliability at a higher density. In particular, the valve foil can be forced by the body fluid into the second opening, through the sleeve attachment which is present around all sides of the second opening, only to a defined maximum depth. The depth depends both on the relative area of the surface of the valve foil bounded by the attachment line in relation to the area of the sleeve bounded by the attachment line (or, if present, the auxiliary attachment line), and on the elasticity of the valve foil and the sleeve. If the valve foil and/or the sleeve is under internal tensile stress due to the attachment, the maximum depth is also dependent on the internal tensile stress.

It is advantageous if the aperture of the valve foil has an area between 5 mm$^2$ and 500 mm$^2$. It is particularly advantageous if the aperture has an area between 10 mm$^2$ and 200 mm$^2$. It is also possible that the valve foil has a plurality of apertures, all of which lie outside of the second opening when the second opening is covered. In this case, the apertures of the valve foil together preferably include a total area of between 5 mm$^2$ and 500 mm$^2$, and particularly preferably between 10 mm$^2$ and 200 mm$^2$ (wherein a single aperture of the plurality of apertures preferably has an area of between 0.25 mm$^2$ and 250 mm$^2$, and more preferably between 1 mm$^2$ and 20 mm$^2$). This (total) aperture area enables, on the one hand, a high degree of tightness of the check valve, and on the other hand a low flow resistance for the fluid being conveyed. The attachment line can then, for example, run around all of the apertures together.

According to another aspect of the invention, the check valve can include an additional foil, which lies partially flat against the valve foil, and is attached (in a fluid-tight manner) to the sleeve, wherein the attachment line of the valve foil together with the attachment line of the additional foil surrounds the second opening. The second opening is then surrounded by the attachment lines of the valve foil and the additional foil. Such a foil valve can be configured as an outlet valve, for example, in accordance with DE 35 25 165 A1 which is incorporated herein by reference.

Preferably, the sleeve is, at least partially, exactly or substantially radially symmetric or rotationally symmetric (infinitely radially symmetric) about a longitudinal axis—particularly beyond its ends, or at least its outer envelope ends—in particular with a cylindrical shape, and the second opening is arranged in a shell surface (surrounding the longitudinal axis), particularly a cylinder shell surface, of the sleeve. The smallest outer diameter corresponds to the cross-section along the longitudinal axis. The higher the degree of radial symmetry is, the smaller can be the smallest outer diameter, in an advantageous manner. It is expedient to arrange the third opening on the longitudinal axis.

The sleeve preferably includes (in addition to the line segment) a pump chamber segment. One or more connecting segments can be arranged between the line segment and the pump chamber segment. The pump chamber segment can be wholly or partially a subsegment of the line segment. Advantageously, the first opening of the sleeve is arranged in the region of one end of the line segment, and the second opening is arranged in the region of an opposite end of the line segment.

According to an aspect of the invention, the second opening is arranged in the region of the pump chamber segment of the sleeve. In this case, the pump chamber segment forms a part of the line segment such that the pump chamber is part of the line.

However, in an embodiment which is particularly suitable for use in the left heart, the second opening can also be arranged outside of the pump chamber segment in the line segment.

Typically, the sleeve has a greater inner diameter in the region of the pump chamber segment than in the region of the line segment.

The sleeve can be configured as one piece or several pieces. In one embodiment where there is a plurality of parts, the sleeve can advantageously be constructed of a part arranged outside of the frame, which furnishes the line segment, and a part arranged in the region of the frame, which provides the pump chamber segment. In one embodiment where the sleeve has a plurality of parts, the same can consist of different materials and be advantageously connected to each other in a fluid-tight manner. The sleeve or the parts thereof can also each be made of different materials.

In particular, there can be different materials making up at least two layers. For example, there can be a support layer which gives the sleeve or the part a predetermined mechanical rigidity and an envelope layer connected to the carrier layer to form the fluid-tight sleeve. If the frame is formed by the sleeve itself, the support layer can be formed by the frame.

The sleeve is preferably formed at least in the pump chamber segment by at least one sleeve foil. The sleeve foil can itself be multilayered. Preferably, the sleeve foil is at least locally (directly or indirectly—see above) connected to the frame. Due to its minimal thickness, the sleeve therefore occupies a minimal constructed space. This enables an even smaller outer diameter of the catheter (in the collapsed configuration of the frame) in the region of the pump chamber. The sleeve foil can be routed, for example as in a tissue, back and forth between the internal space and the external space through the struts of the frame.

The sleeve foil in this case can advantageously be deflected (relative to the frame) only to a lesser degree than the valve foil (with identical deflection force) and/or is subject to a greater internal tensile stress by the frame than the valve foil, particularly wherein the elasticity of the sleeve foil is less than that of the valve foil. This achieves, on the one hand, a good seal of the check valve, and on the other hand a low flow resistance for the conveyed fluid.

In all embodiments, the valve foil (and optionally the additional foil) can preferably be arranged inside the sleeve, in such a manner that the check valve functions as an intake valve. This configuration is particularly advantageous for use in the bloodstream in the right heart.

Alternatively, in all embodiments, the valve foil can be arranged outside of the sleeve in such a manner that the check valve functions as an outlet valve. The advantages of the invention are achieved in this way as well.

In an advantageous embodiment variant, the third opening of the sleeve is formed in such a manner that a drive, in particular a balloon of a balloon catheter, in particular an IABP, can be pushed through the third opening into the internal space of the sleeve to a predetermined target position relative to the sleeve. Preferably, the predetermined target position corresponds to the region of the pump chamber segment of the sleeve. The drive can be advantageously pushed through the third opening in such a manner that the same is closed off (in a fluid-tight manner, in particular at least relative to a maximum blood pressure). A catheter according to U.S. Pat. No. 5,460,607 A can be used as the drive, in the form of a displacement device, for example. U.S. Pat. No. 5,460,607 A is incorporated herein by reference.

The drive arranged in the internal space can be connected to an external energy source via a line leading through the third opening—in the case of a balloon catheter, for example, via an auxiliary fluid line to a pump console which can preferably fill and empty the balloon with an auxiliary fluid in a pulsing manner. Due to the displacing effect of the filled balloon, the pump console acts as a drive for the check foil valve according to the invention, and thus enables a directional transport of the body fluid. The drive can be adjusted with regard to the frequency of the filling operations of the balloon with auxiliary fluid and/or the volume of the auxiliary fluid per filling, for example. According to the invention, alternative embodiments of the drive can also be used—for example drives based on the principle of a piston pump or an impeller pump or drives based on the principle of a centrifugal pump.

According to an aspect of the invention, a balloon (a balloon catheter, in particular an IABP) is arranged in the internal volume of the sleeve, and a line for an auxiliary fluid is connected to the balloon for the (reversible) inflation of the balloon, wherein the line for the auxiliary fluid runs outward through the third opening of the sleeve. The third opening is then closed off in a fluid-tight manner by the line for the auxiliary fluid. As a result, the catheter is ready for use, without the additional steps of the subsequent introduction of a separate displacement device into the conveyed fluid, and the insertion of the balloon into the internal space of the line. The duration of treatment is reduced in this manner. In particular, the line for the auxiliary fluid can be connected, or is connected, to a pump (pump console) for the auxiliary fluid.

The frame is substantially tubular in design. Preferably, the frame is, at least partially, exactly or substantially radially symmetric or rotationally symmetric (infinitely radially symmetric) about a longitudinal axis—particularly beyond its ends, or at least its outer envelope ends—in particular with a cylindrical shape. In the catheter according to an aspect of the invention, the frame is preferably arranged at least partially along the region of the pump chamber segment of the sleeve. The frame is preferably deployable. The term "deployable" in the context of the invention means that the frame can be switched between two configurations with different internal volumes. Switching to the configuration with a greater internal volume can be called "deploying" and the other configuration can be called "folded." In particular, the frame can be a deployable stent. The frame can be arranged in the internal space of the sleeve or on the outside around the sleeve. The frame can also be formed by the sleeve itself.

It can be advantageous if the frame forms (rigidly) at least a part of the sleeve, in particular the pump chamber segment, as well as the third opening, and particularly also the second opening. As a result, no additional material, which adds thereto, is needed for the sleeve.

The frame can advantageously include a composition which has a shape memory alloy, particularly nitinol, a shape memory polymer or a shape memory ceramic, or consists of the same. In particular, the ability to switch between the configurations can be reversible.

In a configuration with a greater internal volume, the frame tensions the sleeve in the region of its pump chamber segment to form a pump chamber. The fluid can be transported through the sleeve along the line implemented by the line segment either from the first opening to the second opening or vice-versa.

The transport direction depends on the orientation of the check valve arranged at the second opening.

The check valve can advantageously include a group of several second openings, wherein these openings of the respective group can be fully covered by the valve foil. This makes it possible to increase the fluid tightness and reduce the resistance to flow. The attachment line can then run around all of the second apertures of the group in question.

Particularly preferred are embodiments in which preferably a plurality of second openings is arranged, each with a check valve, in the shell surface of the substantially cylindrical sleeve, and in each of these is arranged a valve foil or a segment of the valve foil defined by lines of attachment, each with an aperture or a group of apertures (belonging to the respective check valve in question) to cover the respective second opening. In this way, the flow resistance of the catheter line can be reduced, with increased tightness.

Also advantageously, each check valve can include a group of several second openings, wherein the openings of the respective group of second openings can be fully covered by a valve foil or a segment (defined by an attachment line) of the valve foil. In this way, the flow resistance of the catheter line can be reduced, with increased tightness. The attachment line belonging to a group can then run, for example, around all of the respective second openings belonging to the group.

Preferably, a further valve, in particular a check valve, is arranged in the line for the body fluid or at the end of this line, which acts opposite to the at least one first valve. This improves the efficiency of the directional transport.

The line is preferably flexible, and particularly is a flexible tube.

The line for the body fluid has an elastic spiral at the end which is remote from the frame. In this way, the line end can be held at a predetermined position in the body, and particularly can be fixed in the blood vessel with a spacing therefrom on all sides.

Preferably, each second opening has an area of between 5 mm$^2$ and 500 mm$^2$.

It is particularly preferred that each second opening has an area between 10 mm$^2$ and 200 mm$^2$. In the event that the check valve includes a group of second openings, each group of second openings belonging to one check valve has a total area of between 5 mm$^2$ and 500 mm$^2$, and more preferably between 10 mm$^2$ and 200 mm$^2$ (wherein a single opening of the group of second openings advantageously has an area of between 0.25 mm$^2$ and 250 mm$^2$, and more advantageously between 1 mm$^2$ and 20 mm$^2$). This (total) opening area enables, on the one hand, a high degree of tightness of the check valve, and on the other hand a low flow resistance for the conveyed fluid.

The first foil and/or the second foil can advantageously be made of at least one polymer, in particular polyurethane, in particular with a foil thickness of between 0.01 mm and 0.2 mm. This enables a first configuration of the catheter with a minimum constructed space.

According to the invention, the line segment comprises a film tube with a reinforcement running in the interior of the film tube, wherein the film tube has a foldable section, a connecting region in which the film tube is connected to the reinforcement, and a stabilized section with a structuring.

The property "foldable" means, in the context of the invention, that the film tube which is dimensionally stable up to a predetermined (relative) threshold low pressure relative to an external pressure, is not stabile at pressures lower than the threshold low pressure, wherein the instability arises at a relative pressure difference $\Delta P$ between the interior and the exterior of less than −500 mm Hg, and preferably less than −200 mm Hg.

As a result of the fact that the body fluid transporting section (line segment) of the catheter comprises a film tube, the catheter can have a greater internal diameter (preferably greater than 7 mm, and more preferably greater than 8 mm) in this section than in the prior art, such that the amount of fluid which can be transported through the catheter interior per time unit can be significantly higher than in the prior art. The foldable section makes a reversible folding state possible, which enables a minimally invasive insertion of the catheter into the body in spite of an inner diameter of the distal section which is larger than in the prior art. This is particularly advantageous in the field of cardiology since experience shows that a reduced implantation diameter of the cardiac catheter results in fewer patients of a particular patient population needing to be excluded from a procedure on account of their individual vessel inner diameter, and/or a higher fraction of patients can be directed to acute care without an additional vascular specialist needing to be present for support. In addition, the safety of the implantation and explantation can be improved by the smaller implantation diameter. For applications in cardiology, wherein the catheter is inserted, for example, in a minimally invasive manner into the heart via a groin vessel, the catheter can be advanced into the heart, and particularly in the region of a heart valve, in a manner which is significantly gentler to tissue than has been hitherto possible with conventional cardiac catheters, due to the foldable section.

The foldable section can comprise the line segment.

The foldable section is preferably folded when ready for use (that is, when able to be inserted into the body). This allows a further improvement in insertability into the patient's body. The folding can be random, or "ordered" in a predetermined pattern, and/or along predetermined fold lines. For example, the film material of the foldable section can be folded in a spiral or along one or more longitudinal folding lines. The folding can be maintained by a removable insertion sleeve which is pushed over the foldable section. This makes it possible to advance the catheter, when the foldable section is folded (compressed), via an access point at its determined point of entry in the body, and then to unfold the same by removing the insertion sleeve.

The connection of the film tube to the reinforcement and/or to an adjacent catheter section can be realized, for example, by welding (by way of example, cold welding or ultrasonic welding), or by gluing.

The stabilized section has an increased buckling resistance. In other words, the stabilized section has increased dimensional stability. In this way, once the catheter has been inserted into the body, it is possible to effectively prevent the film tube from buckling, for example at a place where the tube travels a tight loop due to anatomical/physiological conditions. Such a buckling is undesirable because the inner tube cross section which is reduced as a result of the buckling point can significantly reduce the amount of body fluid which can be transported through the film tube per unit of time. By way of example, if the catheter is inserted in the right heart for a procedure, the film tube can be arranged inside the right ventricle, with its distal end extending into the pulmonary artery. In this case, the film tube inscribes a tight loop in the right ventricle. It is possible to effectively prevent the tube from buckling at this point by means of a corresponding sectional stabilization of the film tube in the region of the loop.

As will be described below in more detail, the catheter can be advantageously configured for a pulsatile mode. The pressure fluctuations typically associated with pulsatile operation likewise do not lead to a (complete) buckling of the stabilized section. As such, the operational reliability of the catheter is significantly improved overall.

The foldable section can comprise the stabilized section.

The structuring of the stabilized section can preferably be a rib-shaped profiling. This enables effective stabilization in a simple manner. The buckling resistance can be adjusted by the configuration of the rib size, the rib spacing, et cetera. The ribs can be, by way of example, arranged transversely to the longitudinal direction of the film tube, or in a spiral. In an arrangement transverse to the longitudinal direction of the film tube, the ribs are each closed rings. In a spiral arrangement, one or more ribs are arranged in a coil form in the longitudinal direction of the film tube. Additionally or alternatively, it is possible that the film of the film tube is made thicker within the stabilized section, for example thicker by one-fifth or by one-half, than in an adjacent section.

Advantageously, the catheter can be configured in such a manner that the body fluid is suctioned through the first port into the internal volume (above and hereinafter also referred to as the catheter interior), conveyed in the internal volume in the distal direction, and discharged through the second port out of the internal volume. The configuration for transporting the body fluid in the distal direction of the catheter is particularly suitable for applications which support the pumping power of the right heart. The ports in this case are advantageously arranged in such a way, and the length of the film tube is configured in such a manner that, the catheter is inserted percutaneously into the human body and into the right heart via a central vein, the first port is positioned in the region of the right ventricle and the film tube extends from the right ventricle into the pulmonary artery, such that the second port is arranged in the pulmonary artery. As such, for the purpose of supporting the right ventricle, blood can be taken up in the right ventricle into the catheter, conveyed directionally in the internal volume to the region of the pulmonary artery, and discharged at that point out of the catheter. According to another advantageous embodiment, the right heart is bypassed by the line segment of the catheter. In this case, the first port lies in front of the right heart in the flow direction of the blood stream, for example in the inferior vena cava, the point where blood is taken up and transported through the entire right heart in the internal volume, then discharged out of the catheter through the second port in the pulmonary artery.

The film tube has a length of between 10 cm and 30 cm, preferably between 15 cm and 20 cm, and is ideally about 17 cm long; this is especially true in cases where the catheter is intended for use in the right heart.

The film tube has a wall thickness of particularly less than 0.6 mm, and preferably less than 0.3 mm.

The material of the film tube can comprise a plastic, preferably an elastomer such as a polyurethane, or a thermoplastic such as polyethylene. The material should be suitable for intracorporeal applications.

As previously explained in detail, the catheter according to the invention can thus have a film tube which is divided into sub-sections, wherein the sub-sections can, for example, each differ from each other in wall thickness (within the above range), material composition, material density, buckling resistance, pressure resistance, diameter and/or structuring of the inner and/or outer surface.

Preferably, the film tube is exactly or substantially radially symmetric or rotationally symmetric (infinite radial symmetry) about a longitudinal axis, at least in sections, particularly outside of its ends, and in particular is cylindrical, and the first port and/or the second port is/are arranged in a shell surface (surrounding the longitudinal axis), in particular a cylinder shell surface, of the film tube. The least outer diameter then corresponds to the cross section of the longitudinal axis. Higher-order radial symmetry advantageously leads to smaller least outer diameters.

The reinforcement is advantageously established by a guide tube, for example a commercially available angiographic catheter or the like, which has a further lumen (hereinafter also referred to as the tube interior). Preferably, the guide tube has an outer diameter between 0.5 mm and 2 mm.

Preferably, the guide tube is configured to be moved via a guidewire for the intended positioning of the catheter. Because the reinforcement additionally assumes the function of a guide tube which can be moved via a guidewire, the catheter can be implanted using the Seldinger technique known in cardiology, for example. In this case, the catheter preferably has a third proximal port, and the guide tube runs from this proximal port through the catheter to the second port. The distal end of the guide tube can pass through the second port. The tip of the guide tube is preferably curved back.

The distal end of the guide tube advantageously comprises a medication port. Alternatively or additionally, an (additional) medication port can also be arranged in the area of the second port. The medication port connects the tube interior (of the guide tube) to the outside, such that the inside of the tube communicates via this medication port with the exterior. In this way it is possible to administer a medication to the body via the guide tube when the catheter has been inserted into the body, the medication being discharged from the catheter through the medication port, by way of example locally in the area of the body which surrounds the medication port, and being able to achieve its effect in a faster and/or more targeted manner.

Advantageously, the film tube can have a plurality of second ports. The second ports can be at least partially arranged at a distance from the distal end of the film tube. By providing a plurality of second ports, their (total) port cross-section can be effectively increased, such that the body fluid transported distally can be released with lower local pressures from the catheter interior. The forces acting on the film tube, the body fluid, and the body tissue surrounding the second ports can thus be reduced advantageously.

The film tube preferably has a distal section which is particularly expanded bulbously, with an average outer diameter which is enlarged (relative to the adjacent section), and the second ports are arranged distributed within this section. Such an arrangement of the second ports results in the body fluid exiting the catheter in different directions, so that the forces acting on the film tube, the body fluid, and the body tissue surrounding the second ports, in particular in the case of a non-continuous, pulsatile—that is, surging and/or intermittent—transport of the body fluid can be further reduced, wherein it is particularly possible to prevent a "beating" of the distal end of the film tube due to the pressure fluctuations associated with the pulsatile transport (systole and diastole in the use of the catheter as a heart catheter).

The catheter preferably includes (in addition to the line segment) a pump chamber section. One or more connecting sections can be arranged between the line segment and the pumping chamber section. The envelope of the pump chamber section can be formed by the film tube. The pump chamber section can be wholly or partially a subsection of the line segment. The pump chamber section can be wholly or partially a subsection of the foldable section. Appropriately, the first port is arranged in the region of one end of the line segment, and the second port is arranged in the region of an opposite end of the line segment.

In a preferred embodiment, the first port is arranged in the region of the pump chamber section. In this case, the pump chamber section forms a part of the line segment, such that the pump chamber is a part of the line.

In a further suitable embodiment, however, the first port can be arranged outside of the pump chamber section in the line segment.

Typically, the catheter has a larger inner diameter in the region of the pump chamber section than in the region of the line segment adjoining the pump chamber section area. In particular, the pump chamber section has an average internal diameter greater than 15 mm.

The pump chamber section can include a pump chamber. The pump chamber preferably has a (deployable) frame. The material of the frame preferably comprises a composition comprising a shape memory alloy, in particular nitinol, a shape memory polymer, or a shape memory ceramic. The frame has a substantially tubular configuration. Preferably, the frame is exactly or substantially radially symmetric or rotationally symmetric (infinite radial symmetry) about a longitudinal axis, at least in sections, particularly outside of its ends, or at least its outer sleeve ends, and in particular is cylindrical. In particular, the frame can be a deployable stent. In other words, the pump chamber section or at least the pump chamber can be foldable. The foldable section can thus include the pump chamber section and/or the pump chamber. The frame is preferably arranged in the interior of the pump chamber.

The pump chamber is preferably between 150 mm and 300 mm long.

The catheter preferably has a third port in its proximal region, such that a drive, in particular a balloon of a balloon catheter, in particular of an intra-aortic balloon pump catheter (IABP), can be passed through the third port into the interior of the catheter up to a predetermined final position relative to the catheter. The predetermined target position preferably corresponds to the pump chamber—that is, the balloon is preferably intended to be arranged in the pump chamber.

The drive can expediently be passed through the third port in such a manner that the same is closed off in a fluid-tight manner (that is, particularly at least with respect to a maximum blood pressure). A catheter according to U.S. Pat. No. 5,460,607 A can be used as the drive in the form of a displacement device, by way of example. The drive arranged in the interior can be connected to an external power source via a line leading through the third port—in the case of a balloon catheter, for example, via an auxiliary fluid line to a pump console (pump) which can fill and deflate the balloon with an auxiliary fluid, preferably intermittently. A directional transport of the body fluid is made possible by the displacing effect of the filled balloon. By way of example, the drive can be adjustable with respect to the frequency of the filling processes of the balloon with auxiliary fluid and/or the volume of the auxiliary fluid per filling.

In a particularly advantageous embodiment variant, the catheter is constructed in such a manner that the catheter has a pump chamber in which the balloon of an IAB catheter is permanently disposed. By means of a line for an auxiliary fluid which passes through the third port of the catheter to the outside, the balloon can be connected to an external pump, particularly a so-called IABP pump console. As such, the catheter is ready to use, without the additional steps of a subsequent introduction of a separate displacement device into the fluid being conveyed, and the insertion of the balloon into the interior of the line catheter. The implantation time is thereby reduced.

Helium is preferably used as the auxiliary fluid for filling the balloon.

A non-return valve can be arranged at the first port and/or the second port (to allow only unidirectional flow between the internal volume and the external space surrounding the catheter). The non-return valve is preferably configured as a diaphragm valve according to DE 10 2014 003 153.5, the disclosure of which is hereby incorporated in its entirety into the present invention. A plurality of diaphragm valves is preferably arranged inside the pump chamber section (particularly more than 50 or even more than 100 diaphragm valves). In this case, the individual diaphragm valves are preferably arranged in rows which are equally distributed and which extend along the pump chamber section.

Additionally or alternatively, it is possible that the foldable section and/or a subsection of the foldable section provides a valve function. This is preferably implemented in combination with a pulsatile operation of the catheter, wherein the periodic changes in the pressure conditions in the catheter interior due to the intermittent transport of the body fluid lead to the periodic collapse and subsequent expansion of the foldable section/subsection. By way of example, body fluid in the interior of the catheter can be pumped in a pulsatile manner in the distal direction by means of an inflatable balloon disposed proximally to the foldable section, by the body fluid being displaced distally by the volume increase of the balloon during filling, and escaping from the catheter through the second port arranged distally from the foldable section. The foldable section/subsection is expanded in this case due to the currently prevailing overpressure in the catheter. Subsequently, the balloon is evacuated, thereby producing a negative pressure in the catheter interior, which leads to the collapsing of the foldable section/subsection. As a result of the greatly reduced inner tube cross section in the region of the folding section/subsection, the valve action arises which effectively prevents backflow of distally displaced body fluid in the proximal direction.

BRIEF DESCRIPTION OF THE DRAWINGS

The invention will be explained in more detail below with reference to drawings, wherein:

FIG. 1 shows a known line catheter with conventional check valves according to the prior art;

FIG. 8 shows a second opening with an aperture offset with respect to the same, and with a possible attachment line;

FIG. 9 shows a line catheter with a plurality of inlet foil valves;

FIG. 13 shows an embodiment of the catheter with a bulbous enlarged distal section having a plurality of second ports;

FIG. 14 shows a part of the film tube of a catheter according to the invention, having a distal bulbous enlarged section;

DESCRIPTION OF THE PREFERRED EMBODIMENTS OF THE INVENTION

Figure 2A:
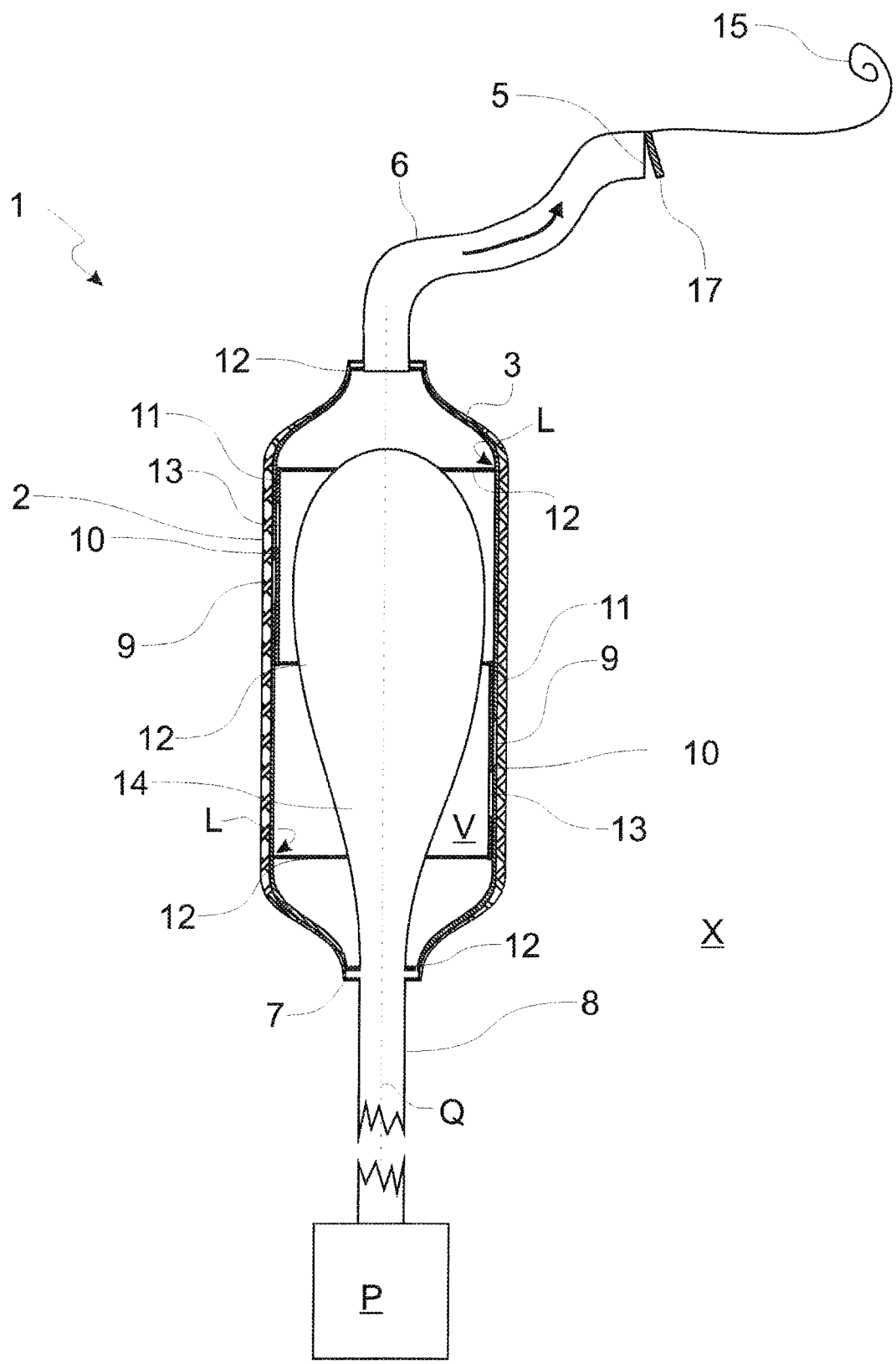
FIGS. 2A and 2B show a line catheter with multiple inlet check valves in the form of foil valves with separate first foils and integrated pump balloons, in two difference states.

FIG. 1 shows a known catheter 1 in a schematic view from the outside. The catheter 1 includes a metal cage as a frame 2. In the interior of the metal cage, a sleeve 3 is arranged in such a manner that it has an internal space (not shown). A balloon (not shown) of a balloon catheter 4 is arranged in the internal space. The sleeve 3 includes, outside of the frame 2, a tube depicted as line 6 for the body fluid to be transported—in this case, by way of example, blood—at the end of which, remote from the frame 2, is arranged a first opening 5. The sleeve 3 has a plurality of second openings (not shown), wherein a check valve with mechanical flaps (not shown) is arranged as an inlet valve on each of the same. Regarding the second openings and check valves and their operation, reference is hereby made to U.S. Pat. Nos. 8,932,246 and 8,409,128, FIG. 4, which are incorporated herein by reference. Finally, the sleeve 3 has a third opening 7 through which the balloon catheter 4 is guided into the internal space of the sleeve 3. The balloon cannot be seen since the illustration is an external view. The sleeve 3 is closed off in a fluid-tight manner with respect to the local external space X. The fluid line 6 is open on the end thereof which faces away from the internal space, such that the fluid is transported from the internal space V through the line 6 and can exit at the end thereof. The second opening of the sleeve 3 is only permeable to fluid in the direction of the inlet, for example. In the opposite direction of flow, the second opening is closed off by the check valve. The third opening 7 of the sleeve 3 is then closed off in a fluid-tight manner by the line 8 of the balloon catheter. This auxiliary fluid line 8 is connected to an extracorporeal pump P which alternatingly pumps the auxiliary fluid into the balloon catheter and withdraws the same therefrom.

The balloon catheter 4 in this case functions as a drive for the line catheter 1 in the form of a positive displacement pump, specifically a diaphragm pump. The general operation thereof is described in U.S. Pat. Nos. 8,932,246 and 8,409,128 which are incorporated by reference.

Figure 2B:
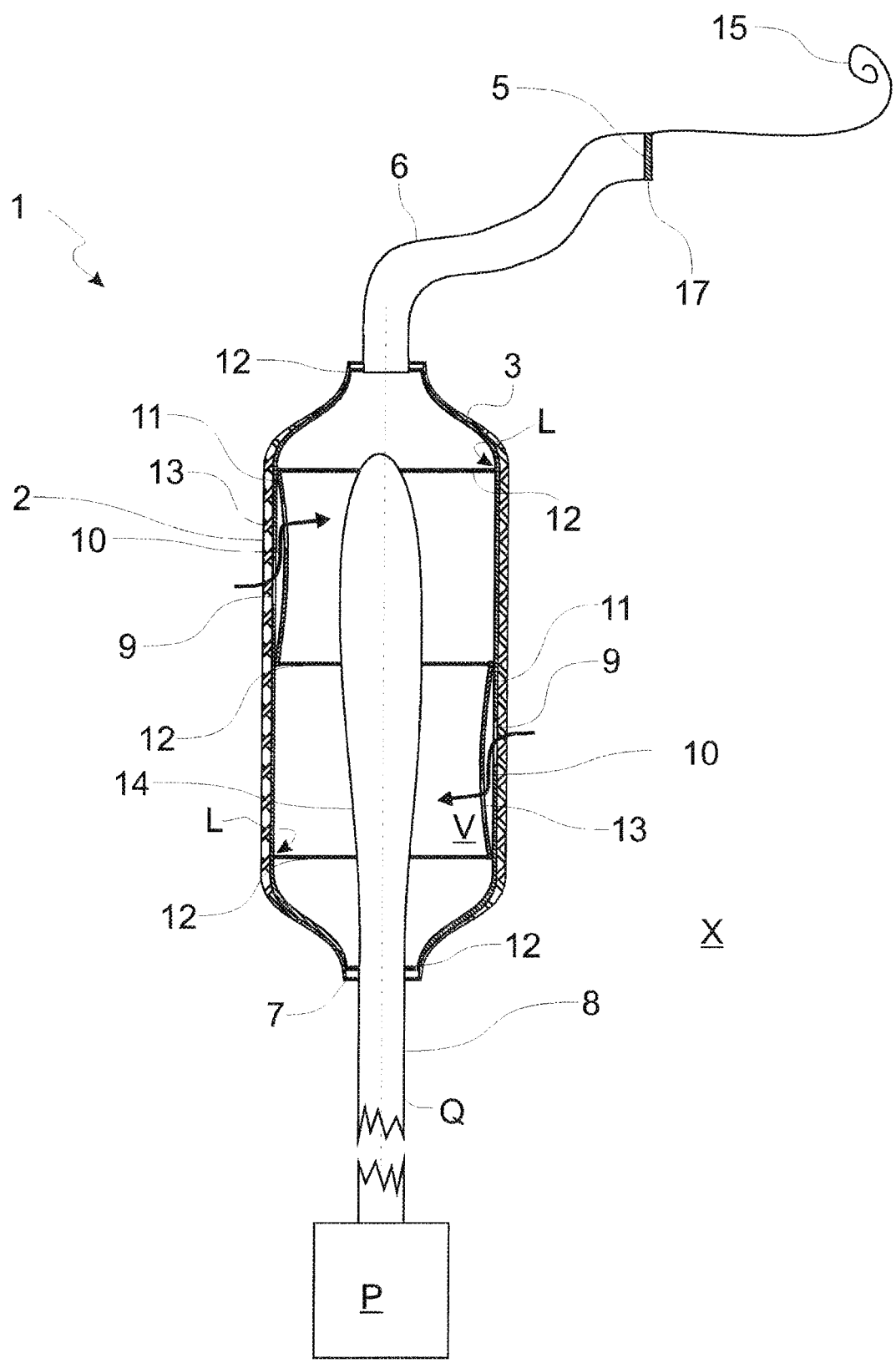

FIGS. 2A and 2B show, in a schematic section view, an improved catheter 1, the construction of which basically corresponds to that shown in FIG. 1. It can preferably be used as a right heart pump catheter. The check valves 10 which are arranged on the second openings 9 of the sleeve 3 are configured as foil valves. To this end, a valve foil 11 is attached to the sleeve 3 by clamping at each second opening 9 by rings 12, along the line L defined by the respective outer diameter of the respective ring. The cover 3, in the form of a sleeve foil which in this case clads the entire frame 2, by way of example, is arranged between the valve foils 11 and the frame 2. It is attached to the frame 2 by the rings 12, likewise by clamping.

The balloon 14 of the balloon catheter 4 is arranged in the internal space V of the sleeve 3, the auxiliary fluid line 8 of which is guided out through the third opening 7 to the pump P.

Due to the clamping against the frame 2, the sleeve foil 3 is only able to be deflected a smaller distance from the frame 2, by a static pressure which is lower in the internal space V than in the external space X, than the valve foil 11, because it is subjected to a greater internal tensile stress by the frame 2 than the valve foil 11, and also has a lower elasticity than the valve foil 11. Each valve foil 11 has an aperture 13 which is offset with respect to the associated second opening 9 of the sleeve foil 3. When there is a static pressure which is lower in the internal space V than in the external space X, the body fluid being transported from the external space X through the openings 9 and the check valves 10 formed by the foils 11 and 3 can flow into the internal space V (the direction of passage, shown by arrows in FIG. 2B). When the opposite pressure condition prevails, for example during the inflation of the balloon 14 by the pump P by means of the auxiliary fluid, the valve foils 11 are pressed against the sleeve 3. Due to the offset between the second openings 9 and the apertures 13, the second openings 9 are covered by the valve foils 11 and thus closed off in a fluid-tight manner (the blocking direction, shown in FIG. 2A). Therefore, the body fluid being transported cannot flow from the internal space V through the opening 9 into the external space X. Rather, it must leave the internal space V through the line 6.

The catheter 1 can switch between two configurations in the segment in which the frame 2 is arranged, which differ in terms of the volume of the internal space V and in terms of the smallest outer diameter of the frame 2. The ability to switch is made possible due to the radially symmetric structure of the frame 2 about the longitudinal axis Q, and its being composed of a shape memory alloy, such as nitinol, as well as the flexible design of the check valves 10 and their arrangement in the shell surface of the essentially cylindrical frame. In the first configuration, the frame is folded such that it has an outer diameter of only 20 Fr at the thickest point. In the second configuration, it is unfolded such that the balloon 14 can be inflated. The frame 2 can be formed by a known, deployable stent, by way of example.

The foils 3 and 11 consist of polyurethane, for example, but can also be made of a different material, in particular another polymer. They are, by way of example, 0.1 mm thick, such that the foil valves 10 each have a thickness of less than 1 mm. All openings 5, 7, 9 of the sleeve 3 are, by way of example, circular with an opening area of, for example 5 mm$^2$, but can have any other shape and different sizes.

The same is true for the apertures 13 of the valve foils 11. The openings 5, 7, 9 and apertures 13 are produced, by way of example, by stamping, but also can be cut with a laser or produced in another manner.

A check valve 17 is arranged, as an outlet valve, at the first opening 5, which is arranged on the end of the fluid line 6 facing away from the internal space V, to improve the line efficiency; and an elastic spiral 15 is arranged, for the purpose of better fixing the line end, in a position with free space on all sides thereof from the vessel wall.

Each foil valve 10 opens and allows a fluid, such as blood, to flow through the outer opening 9 when the valve foil 11, which, apart from the rings 12, is not taut relative to the frame 2, which due to its relative rigidity makes the internal space V into a pump chamber, is drawn somewhat inward by the drive (suction or vacuum effect) of the inner balloon 14 which has just been emptied (in the systole, in the case of an application example of a pump catheter), as shown in FIG. 2B. Because of the briefly-formed channel between the outer opening 9, which is always open, and the inner aperture 13 which is temporarily drawn inward, the fluid can flow into the pump chamber V through the foil valve 10, which is normally operated in a pulsed manner, in a directional, time-controlled manner. In contrast, the foil valve 10 is closed rhythmically in the inflation phase of the balloon 14 (the diastole, in the application example of a pump catheter), as shown in FIG. 2A, when the inner catheter 4, for example an IABP catheter, driven by an external gas flow, is abruptly inflated, and the valve foil 11, due to the pressure increase in the pump chamber V, lies against the sleeve foil 3 cladding the pump chamber V. In this case, the staggered or offset openings 9 and apertures 13 of both foils 3, 11 of the foil valve 10 close, and the fluid, particularly blood, situated inside the pump chamber V, can be pumped directionally in a preferred direction (in the case of a pump catheter, in the distal direction along the line 6). The transport direction is shown by an arrow in the line 6, and/or by arrows in the check valves 10. As such, the foil valves 10, which can be arranged and formed in any arbitrary manner as regards their number and their form on the shell surface of a catheter used inside the body, play a decisive role in making it possible for fluids, preferably blood, to flow directionally in a pump catheter.

Figure 3:
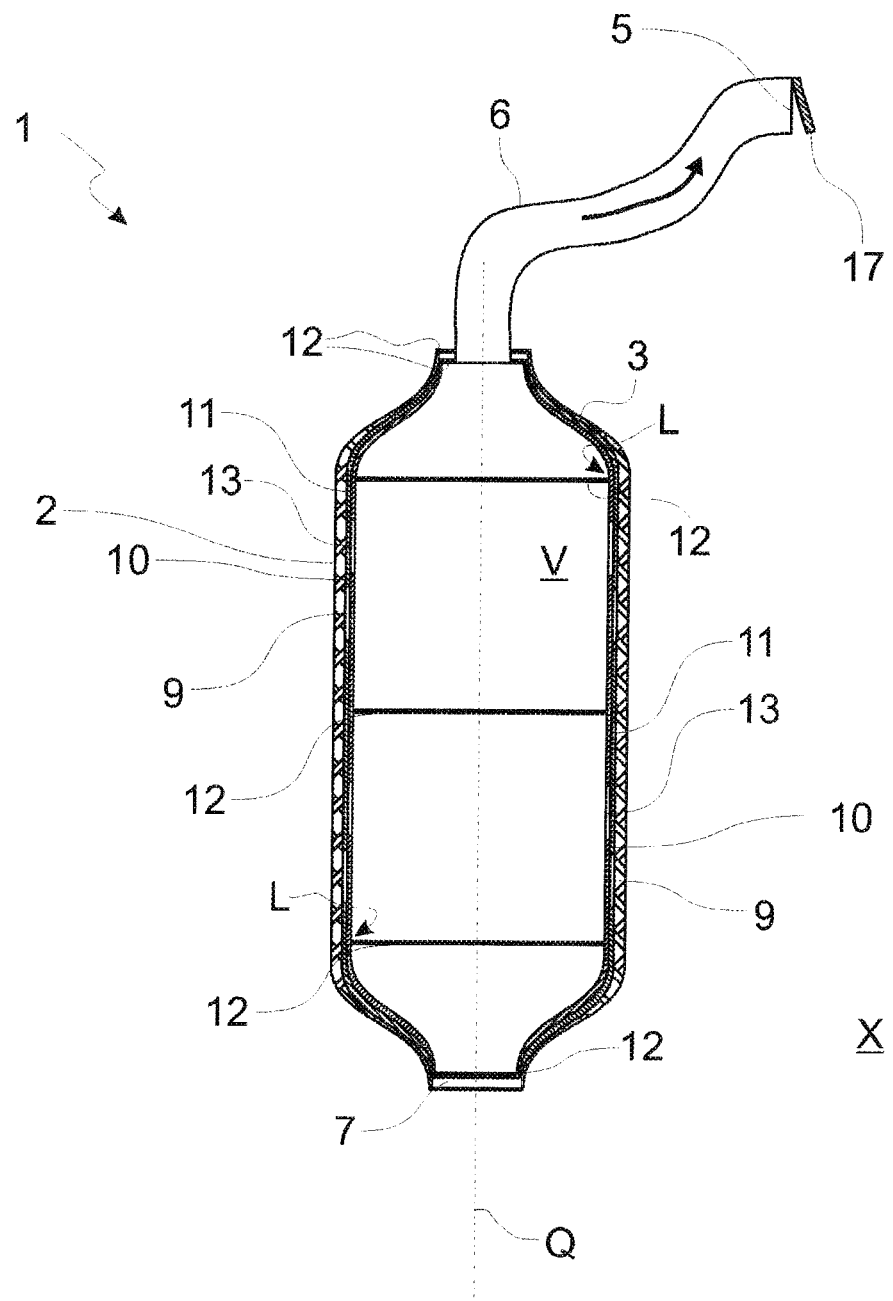
FIG. 3 shows a line catheter with multiple inlet check valves in the form of foil valves with a common first foil.

FIG. 3 shows a schematic segmental view of a line catheter which is modified compared to FIGS. 2A and 2B. In this case, the sleeve 3, which in turn includes a sleeve foil, is clad by a single valve foil 11 which is attached to the sleeve foil by rings 12. The respective segments of the sleeve foil 3 and valve foil 11 between the individual rings 12 differ in their ability to be deflected with respect to the frame 2 when there is low pressure in the internal space V. The segments of the valve foil 11 can be moved further inward than the segments of the sleeve foil 3 by the same force. This is achieved, by way of example, due to a different elasticity or tension or geometry of the foils 3 and 11.

In order to realize the greater deflectability of the first foil 11 in an alternative manner, the first foil 11 can be clamped against the frame 2 with fewer rings 12 than the sleeve 3, by way of example.

In all embodiments, the rings 12 shown can be constructed of, for example, shape memory ceramic, shape memory metal, or as mechanical connection points produced by gluing, clamping or welding of the foil 11 and the sleeve 3. The rings 12 can also be part of the frame 2. Instead of separate rings 12, other geometries can be included—for example a single, continuous spiral. Instead of separate rings 12, there can be regularly or irregularly distributed—by way of example point-shaped—connection points (for example, a plurality of glued or welded points).

Figure 4:
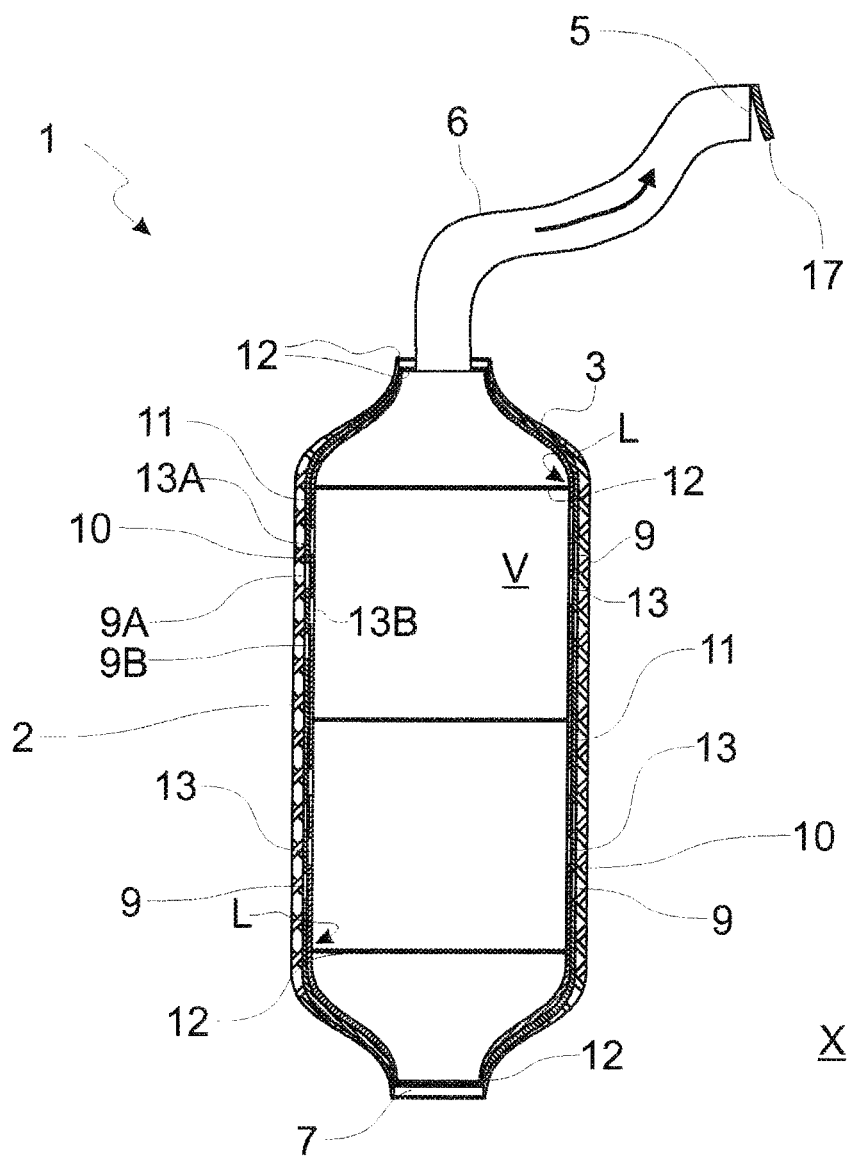
FIG. 4 shows a line catheter with several inlet check valves in the form of foil valves with a common first foil, and for each of these, groups of several apertures and second openings.

FIG. 4 shows a schematic segmental view of an embodiment which is modified compared to FIG. 3. Each check valve 10 in this case includes two second openings 9A and 9B in the sleeve 3, and two apertures 13A and 13B in the valve foil 11 which are offset thereto.

FIG. 5 again shows a schematic segmental view of a line catheter 1 which is modified compared to FIGS. 2A and 2B. It can preferably be used as a left heart pump catheter. In this case, the check valves 10 are formed as outlet foil valves. The valve foils 11 are arranged for this purpose between the sleeve 3 and the frame 2 and again connected to the sleeve at, for example, distributed points, or along an attachment line in the manner of a ring. Because of the additional deflectability of the valve foil 11, the same can, when there is an overpressure in the internal space V, yield into intermediate spaces of the nitinol stent which forms the frame 2, thereby enabling flow from the internal space V through the second openings 9 and the apertures 13 into the external space X. When there is underpressure in the internal space V, the valve foil 11 is drawn against the sleeve 3, thereby covering its second openings 9 in such a manner that the check valves 10 are locked. To support the conveyance efficiency, a check valve 18 is arranged as an inlet valve on the end of the fluid line 6 arranged on the frame 2.

FIGS. 6A and 6B again show a schematic segmental view of a line catheter 1 which is modified compared to FIGS. 2A and 2B. The sleeve 3 in this case is arranged outside of the frame 2 and fixed to it, for example by gluing or welding. The first foil 11 is attached to the outside of the sleeve 3 to implement an outlet valve, for example by a joining method such as welding, soldering or gluing. Alternatively (not shown), it can be attached by clamping rings. In order to realize the opposite transport direction in an alternative embodiment (not shown), the first foil 11 would be arranged on the inside of the sleeve 3 to implement an inlet valve, for example inside the frame 2. The first foil 11 would then be attached on the frame 2 and thus only indirectly to the sleeve 3, or directly to the foil 3 through interstices of the frame 2.

Figure 6A:
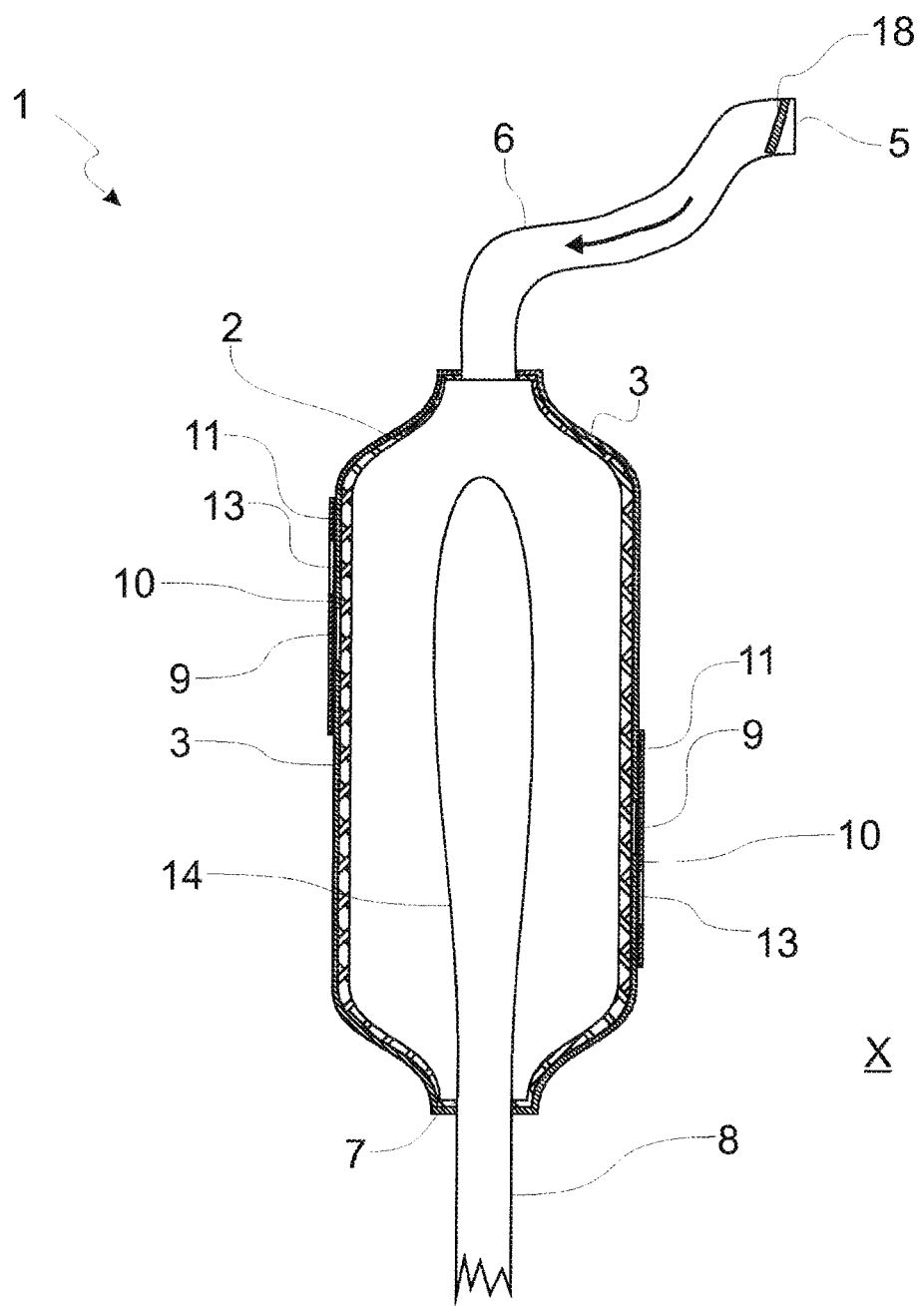
FIGS. 6A and 6B show a line catheter with multiple external outlet check valves in the form of foil valves, in two different states.
Figure 6B:
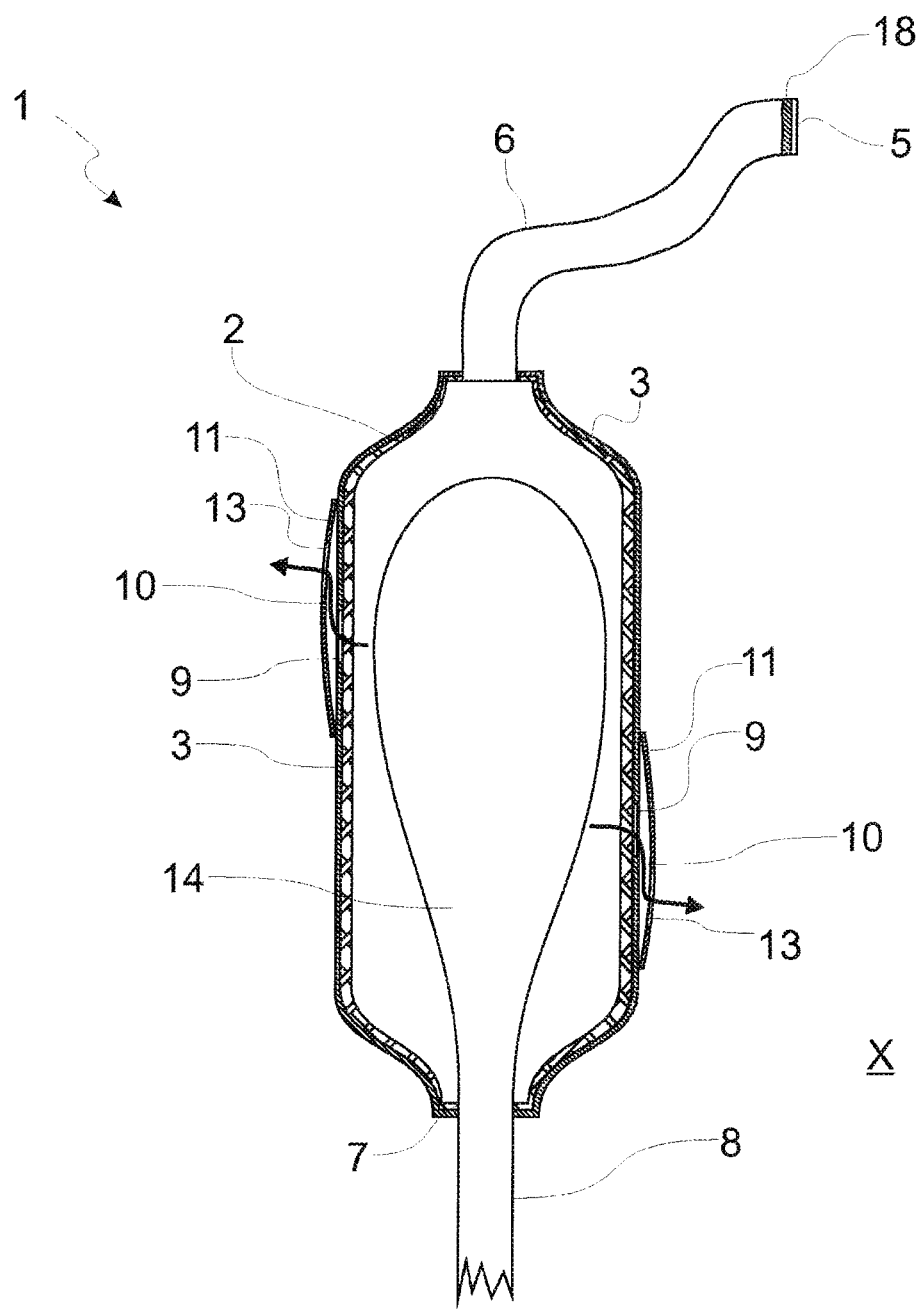

FIG. 6B shows how the fluid during the filling of the balloon 14 is pressed from the internal space V through the outlet foil valves 10, as a result of the first foil 11 being lifted off the sleeve 3 by the fluid. FIG. 6A shows how during the emptying of the balloon 14, fluid is sucked through the line 6 as shown by the arrow.

Figure 7:
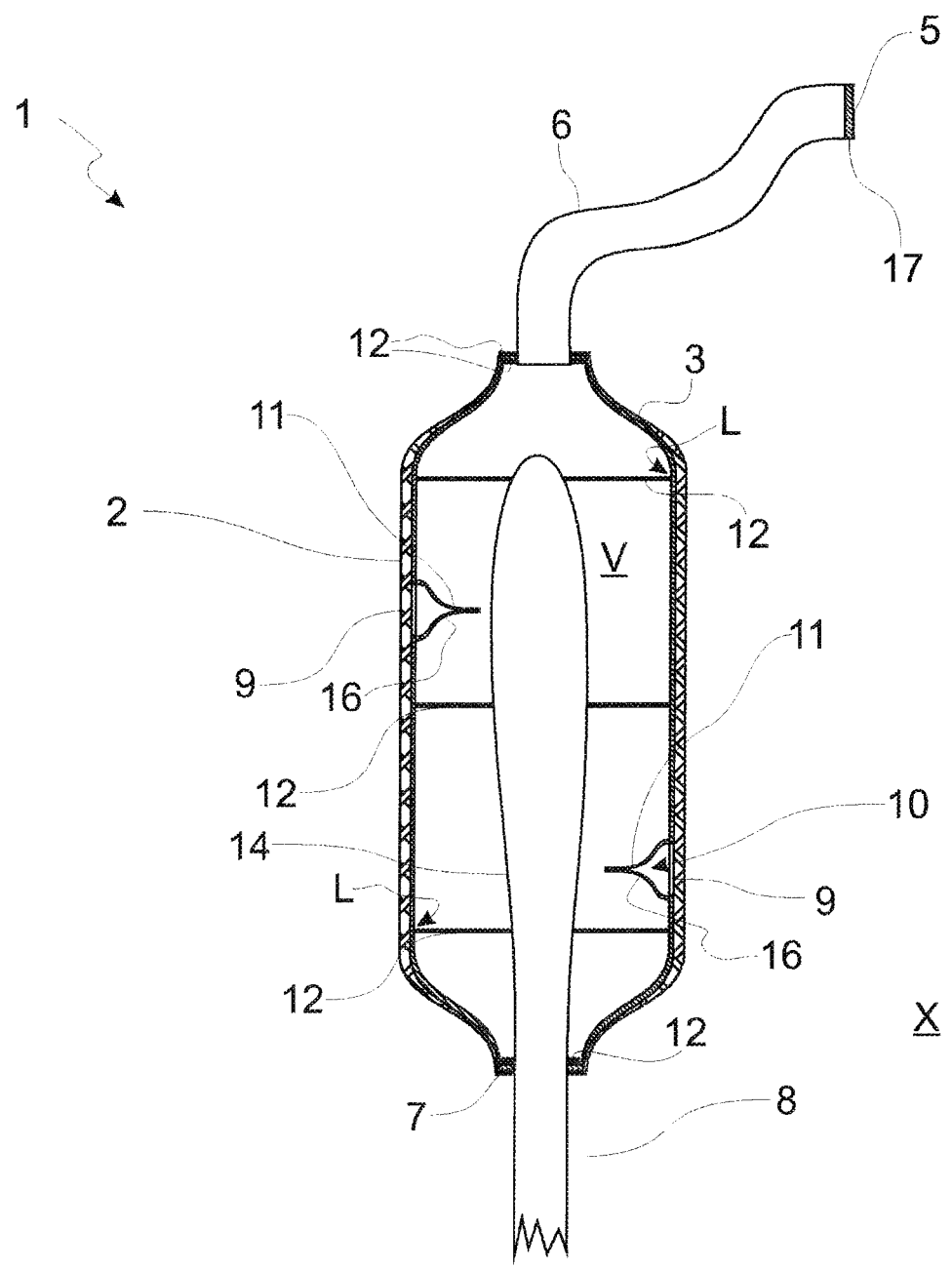
FIG. 7 shows a line catheter with alternative inlet foil valves.

FIG. 7 shows an embodiment with an alternative shape of the foil check valves 10. In addition to a valve foil 11, the check valves 10 have an additional foil 16 which lies partially flat against the valve foil 11. Both foils are attached around the respective second opening 9 to the sleeve 3, which is also made of a polyurethane foil, by way of example. When there is an underpressure in the internal space V, the fluid can push the adjacent sheets 11 and 16 apart and thus flow through the same. When there is an overpressure in the internal space V, however, the two foils 11 and 16 are pressed against each other and are impermeable to fluid, such that no outward flow is possible.

Figure 5:
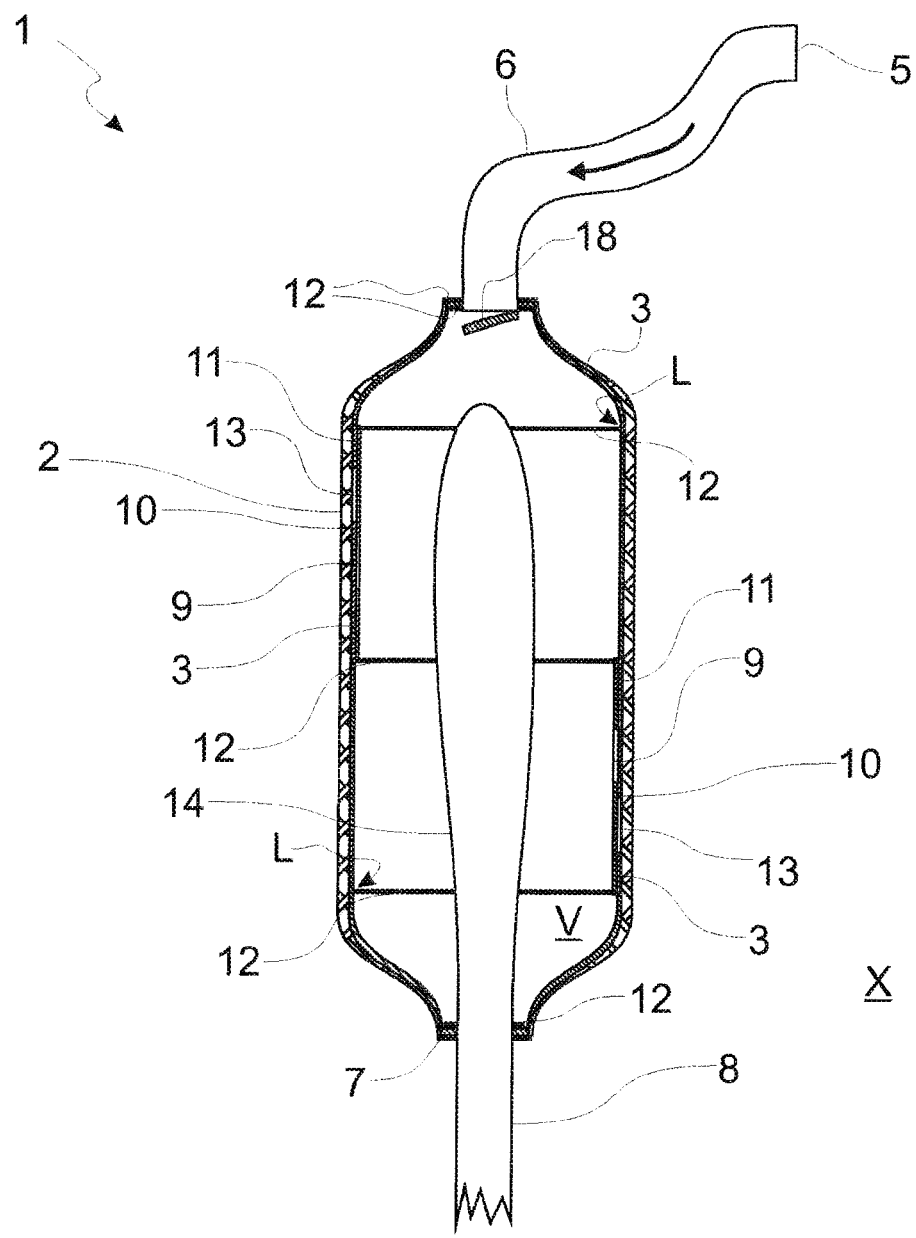
FIG. 5 shows a line catheter with outlet check valves in the form of foil valves.

Such a foil intake valve can be used as a check valve 10 on the end of the fluid line 6 arranged on the frame 2, for example in the embodiment according to FIG. 5. The same configuration of foil check valves 10 can also be used as an outlet valve, in particular in other embodiments—for example according to FIGS. 2A and 2B, at the first opening 5 on the end of the fluid line 6 remote from the frame 2.

In all embodiments, instead of clamping, a different kind of attachment can be used.

FIG. 8 shows a schematic segment of the sleeve 3 with a second opening 9 and the valve foil 11 arranged in front of the sleeve 3, with an aperture 13 offset with respect to the second opening. Around the opening 9 and the aperture 13, together, the valve foil 11 is attached to the sleeve 3 along the line L, for example by gluing or welding.

FIG. 9 shows an embodiment of a catheter 1 according to the invention, having a plurality of foil check valves 10, in a perspective view. The frame 2 is formed by a deployable laser-cut nitinol stent, wherein intermediate spaces are constructed between the individual longitudinal struts of the same. The sleeve 3 is formed by a flexible foil tube. The frame 2 is pushed into the sleeve foil tube 3.

The sleeve tube 3 encompasses the frame 2 tautly, at least in its deployed configuration—that is, with a predetermined pre-tension. The frame thus serves to stiffen the inner volume V formed by the sleeve, which constitutes a pump chamber in the embodiment of FIG. 9, wherein the balloon of a balloon catheter can be placed in said chamber. The sleeve 3 has a plurality of laser-cut or punched second openings 9. The valve foil 11 is likewise a single foil tube with a plurality of laser-cut or punched apertures 13. The valve foil tube 11 is arranged between the sleeve foil tube 3 and the frame 2. The foil of the valve foil tube 11 can be deflected by a given force (corresponding to an underpressure in the internal space V) further into the intermediate spaces of the frame 2 and into the pump chamber than the sleeve foil 3, as a result of its elasticity, which is greater compared to the sleeve foil 3, such that the foil check valves 10 work as inlet valves. The second openings 9 and the apertures 13 are arranged in each case in a spiral around the longitudinal axis Q of the pump chamber. The foil tubes 3 and 11 are oriented with respect to each other such that the spirals of the apertures 13 lie outside of—that is, next to—the spiral of the openings 9, in such a manner that the apertures 13 and the openings 9 are offset relative to each other such that they do not overlap each other. Each opening 9 is therefore assigned to an aperture 13 such that both together form one foil valve 10. The two foil tubes 3, 11 are bonded to each other on their ends along the attachment line L by a glue which is suitable for gluing the foils being applied in a ring shape along the line L. In addition, the two foil tubes 3, 11 are connected to each other in intervals along the longitudinal axis Q. Two spiral adhesive sheets (not shown) are included for this purpose, running on both sides, offset and parallel to the offset spiral paths of the openings 9 and the apertures 13, thus bounding a valve chamber between the two foils, which winds along the longitudinal axis Q around the pump chamber in a spiral. The valve chambers communicate via the openings 9 with the external space X and via the apertures 13 with the internal space V. Their volume when the foil valves 10 are closed—that is, when the valve foil 11 presses against the sleeve 3—is minimal. In the open state—that is, when the valve foil, which is limited in its mobility by the adhesive sheets, is lifted from the sleeve 3 and deflected into the internal space V—the valve chamber has a predetermined volume, the size of which depends inter alia on the given force with which the foil of the valve foil tube 11 is deflected into the pump chamber.

In an alternative embodiment which is similar to that of FIG. 9 (not shown), likewise having also a plurality of foil check valves 10, the frame 2 is again formed by a deployable nitinol stent. The sleeve 3 and the valve foil 11 are again each formed by a flexible foil tube. The frame 2 is pushed into the sleeve tube 3 similarly to the embodiment of FIG. 9. The sleeve tautly surrounds the frame 2, at least in its deployed configuration, such that the sleeve forms a pump chamber V stiffened by the frame 2. The valve foil tube 11 is again arranged between the sleeve foil tube 3 and the frame 2. In contrast to the embodiment of FIG. 9, the openings 9 and apertures 13 are arranged in a plurality of groups, each of six openings 9 and six apertures 13 about the longitudinal axis Q in a ring pattern, offset with respect to each other, such that they do not overlap.

Each opening 9 is assigned to an aperture 13 such that both together form one foil valve 10. In contrast to the embodiment of FIG. 9, the valve foil tube 11 has a greater diameter than the sleeve foil. Because of this allowance, the valve foil tube 11 pushed into the sleeve foil tube forms six pockets in the longitudinal direction Q. The valve foil 11 is adhesively bonded to the sleeve 3 along the six attachment lines L formed by the boundary lines of the pockets, such that six valve chambers are formed along the longitudinal axis Q between the attachment lines L. The valve chambers are arranged in relation to the frame 2 in such a manner that the longitudinal struts of the frame 2 run along the attachment lines L. In other words, the valve chambers are thus arranged in the intermediate spaces running longitudinally between the struts, wherein one second opening 9 of each group of second openings 9 and one aperture 13 of each group of apertures 13 is functionally assigned to each valve chamber. Each valve chamber therefore communicates via the openings 9 assigned to it with the external space X, and via the apertures 13 assigned to it with the internal space V. The volume of the valve chambers is minimal when the foil valves 10 are closed—that is, when the valve foil 11 presses against the sleeve 3. The valve foil 11 then lies substantially—that is, except for the folds that can potentially form due to the allowance—flat against the sleeve foil 3, such that the foil valves 10 are closed off in a fluid-tight manner. In the open state—that is, when the valve foil 11 is lifted by a given force (corresponding to an underpressure in the pump chamber V) off of the sleeve 3 and deflected into the internal space V, the valve chambers then have a predetermined volume, the magnitude of which, inter alia, depends on the force and the allowance.

Figure 10:
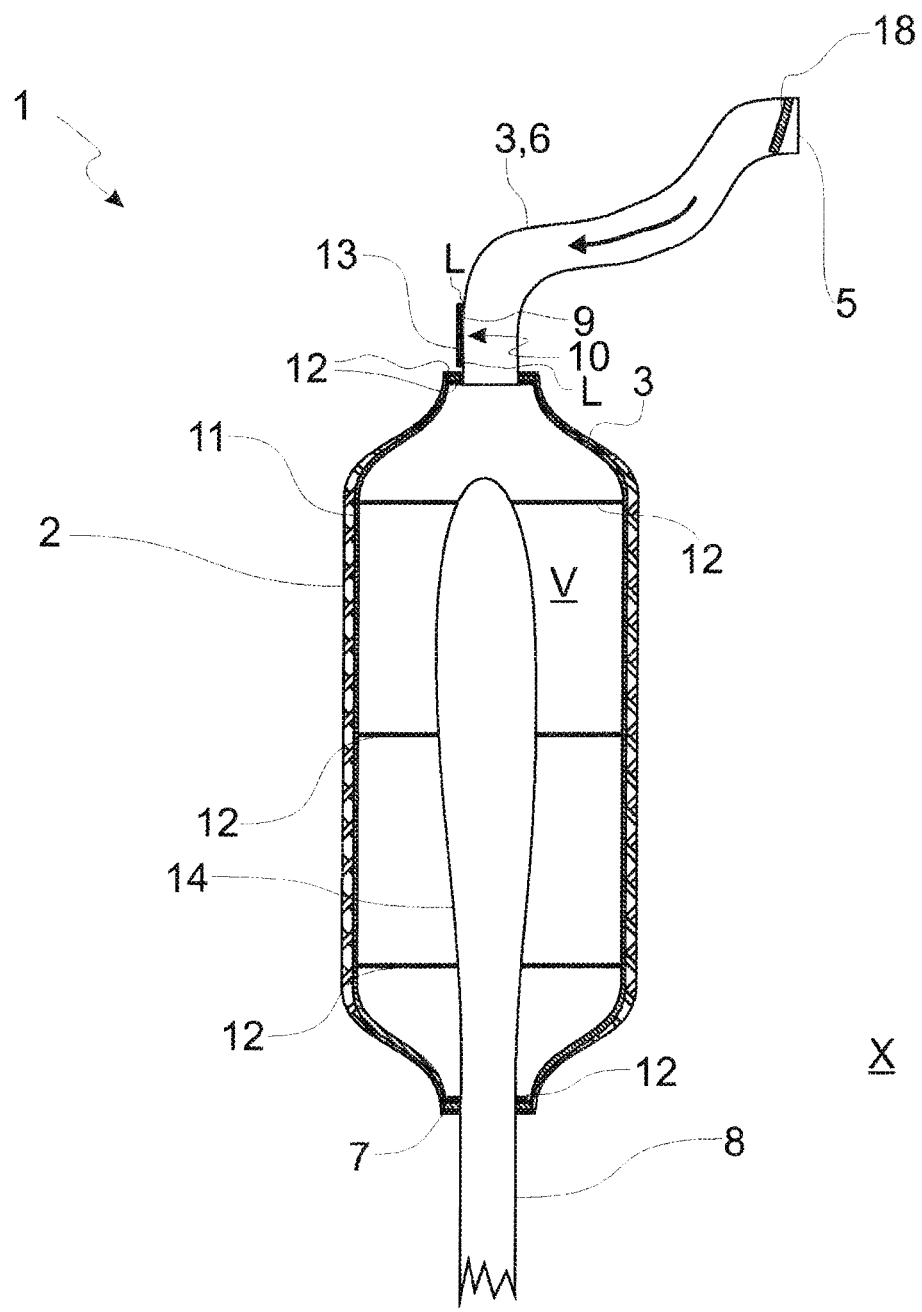
FIG. 10 shows a line catheter with a check outlet valve in the form of a foil valve in the region of the line segment outside the frame.

Finally, FIG. 10 shows a schematic segmental view of a line catheter 1 which is modified compared to FIGS. 2A and 2B. Here, the second opening 9 is arranged in the line 6. The pump segment of the internal space V has no opening to the external space X. A foil outlet valve 10 is implemented on the second opening 9 by a first foil 11 with an aperture 13. An inlet check valve 18 is arranged on the end of the line 6 facing away from the frame 2. If the balloon 14 creates an overpressure in the internal space V, the fluid is forced through the outlet valve foil 10 into the external space X. If the balloon 14 contracts, an underpressure is created in the internal space V such that fluid is drawn through the inlet valve 18 into the line and therefore the internal space V. In the next overpressure cycle, the fluid is then ejected through the outlet valve 10 and thereby conveyed along the line 6.

In all embodiments, a plurality of additional check valves 17 or 18 can be arranged at any point of the line 6, and in particular on the longitudinal axis thereof.

Alternatively or additionally, the additional valve 17/18 or the plurality of valves 17/18 can be arranged outside of the longitudinal axis of the line 6 in the jacket or covering of the line 6.

Figure 11:
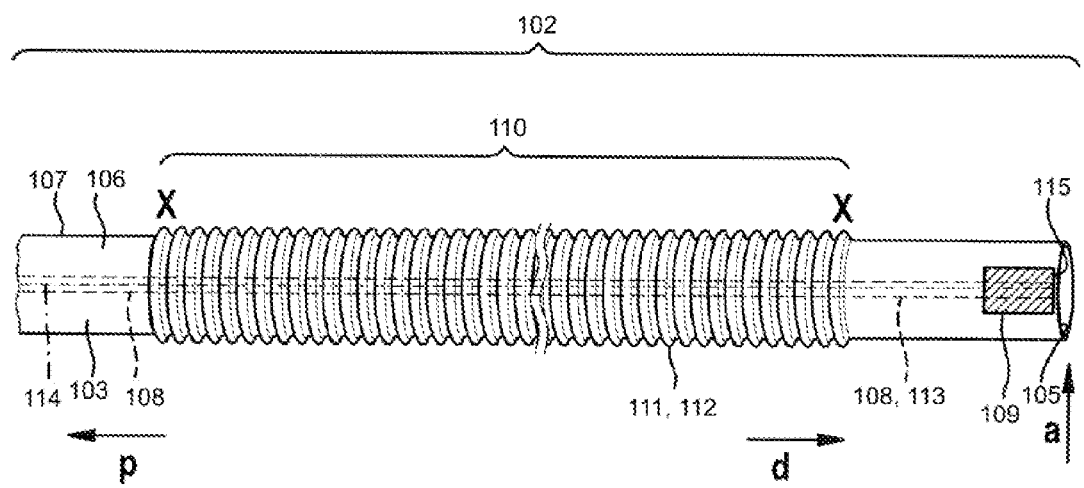
FIG. 11 shows a line segment of the catheter according to the invention, having a film tube which comprises a foldable section which has a stabilized section.

FIG. 11 shows the line segment 102 of a catheter 101 according to the invention. The direction arrows p and d illustrate the distal d and proximal p orientations. The catheter includes a first opening 105, a second opening 104 and a third opening 120. The line segment 102 comprises a film tube 106 which surrounds an internal volume 103. The internal volume 103 communicates with the exterior X via the second opening 104 (shown in FIG. 14) and a first opening 105. The second opening 104 is arranged at the proximal end of the line segment 102 and the first opening 105 is arranged at the distal end of the line segment 102. A reinforcement 108 runs in the interior 103 of the film tube. For clarity, the reinforcement 108 is shown with dashed lines. The reinforcement 108 is connected to the film tube 106 near the distal end of the catheter 101 in a connecting region 109. In the embodiment of FIG. 11, the reinforcement 108 is configured as a guide tube 113. The guide tube 113 is adapted to be moved via a guidewire 114, and for this purpose has at its distal end a tube opening 115. As such, the catheter can be implanted into a patient's body in a simple manner using the Seldinger technique. The film tube has a foldable section 107. In the embodiment of FIG. 11, the foldable section 107 additionally comprises a stabilized section 110. The foldable section is characterized in that it can be packaged in an insertion sleeve (not shown) for better insertability of the catheter into the patient's body. The insertion sleeve has a physiologically favorable outer diameter of, for example, less than 20 French. After puncturing and dilation of a groin vessel the catheter packaged in the insertion sleeve is advanced into the vessel. Then, the insertion sleeve is pulled back out of the vessel, thereby unpacking the foldable section 107. Because of its relative flexibility, the foldable section 107 can then be further advanced to its destination, for example the right ventricle 124, without damaging tissue.

Figure 12:
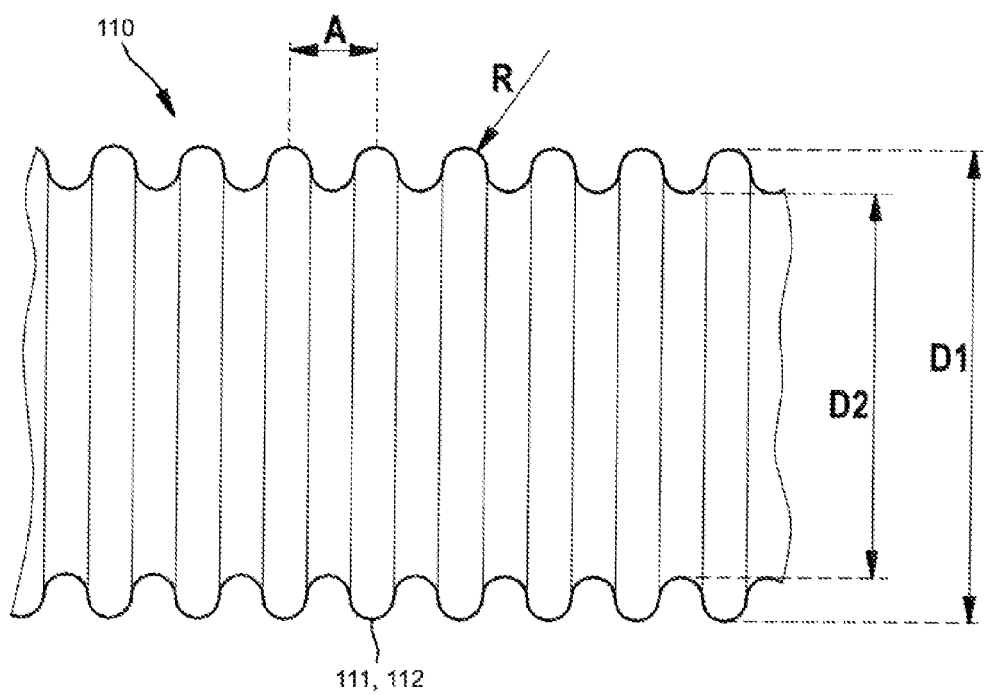
FIG. 12 shows a part of the stabilized section of the film tube according to FIG. 11.

The stabilized section 110 is structured in the form of ribs. This is easily seen in FIG. 12, which shows a section of the film tube of FIG. 11. The ribs are arranged periodically, transverse to the longitudinal direction, in the form of closed rings—that is, not helically. The nominal diameter of the stabilized section corresponds to the diameter at the crest of a rib D1; the core diameter of the stabilized section corresponds to the diameter of a rib base D2. In the embodiment of FIG. 12, the nominal diameter D1 is 9.6 mm, and the core diameter D2 is 8.1 mm. The distance between two ribs (ribs period A) in the present embodiment is 1.6 mm. The radius R of a rib is 0.45 mm.

FIG. 13 shows a further preferred embodiment of the catheter 101, wherein the catheter 101 further comprises a pump chamber section 117 arranged proximal to the film tube 106. The pump chamber section 117 includes a pump chamber 118 and a balloon 121 of a balloon catheter, arranged inside the pump chamber 118. The balloon 121 is connected to a line 122 (FIG. 15) for an auxiliary fluid, which passes to the outside through a third proximal opening 120 (FIG. 15) of the catheter (not shown to improve clarity). The balloon 121 can be connected to an external pump via this line, in particular to a so-called IABP pump console. The balloon 121 can operate in a pulsatile manner—that is, can be filled and emptied with the auxiliary fluid intermittently—and thus serves as a drive for the directional transport of the body fluid. The catheter 101 according to FIG. 13 can thus be advantageously used for intra-aortic balloon counterpulsation procedures. Furthermore, the catheter 101 has a bulbously enlarged distal section 116; 126 which includes a plurality of first openings 105. These are distributed inside the distal section 116; 126 in such a manner that the body fluid transported through the line segment 102 flows out of the first openings 105 in different directions. As a result, the forces acting on the film tube 106, the body fluid, and the body tissue surrounding the first openings 105, in particular in the case of a pulsatile transport of the body fluid, can be reduced, wherein it is particularly possible to prevent a "beating" of the film tube 106 due to the pressure fluctuations associated with the pulsatile transport (systole and diastole in the use of the catheter 101 as a heart catheter).

As can be seen in FIG. 14, the bulbously enlarged distal section 116; 126 can particularly preferably directly adjoin the connecting region 109 proximally. The transition from the connecting region 109 to the distal section 116; 126 can be configured, on the exterior thereof, in such a manner that there is a smooth transition which enables easy advancement of the catheter 101. In the interior of the catheter, the distal section forms a substantially spherical end piece.

Figure 15:
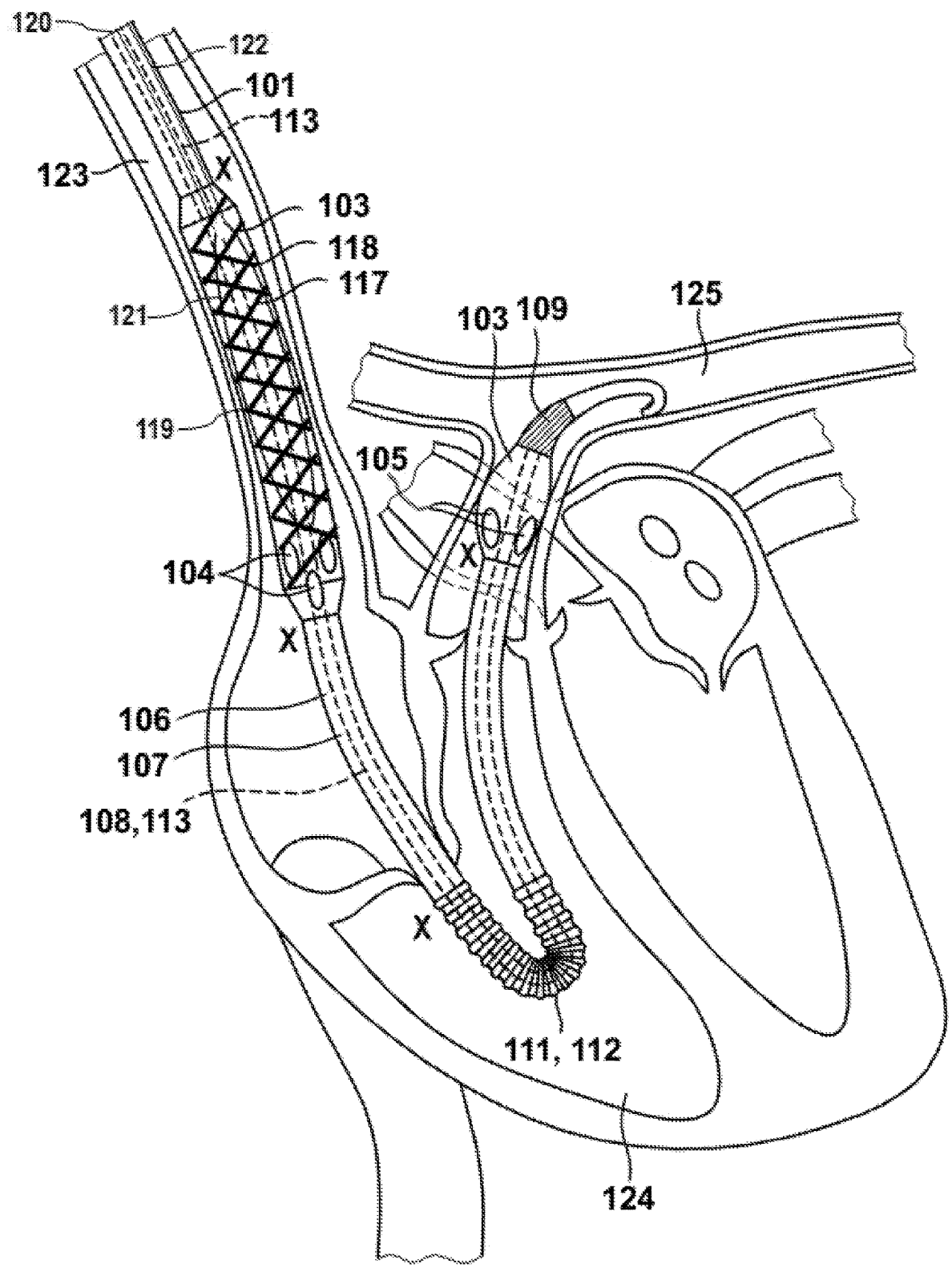
FIG. 15 shows the position of a catheter according to the invention in the right heart of a human patient (access via the superior vena cava), by way of example; and, FIG. 16 shows a further position example (access via the inferior vena cava) of a catheter according to the invention, in the right heart of a human patient.

FIG. 15 shows a typical application of the catheter 101 as a blood pump. For acute cardiac treatment, the catheter is implanted into a patient in a minimally invasive manner via a venous access in the neck. The access via the superior vena cava, as shown in FIG. 15, is purely exemplary in nature, and is only selected in this case for the sake of better illustration. In practice, however, cardiac catheters are often implanted via a groin access. The distal line segment 102 of the catheter is advanced into the right ventricle 124. The pump chamber section 117 with the pump chamber 118 is positioned in the superior vena cava 123. The pump chamber 118 is a part of the line segment 102. The pump chamber is adapted for a pulsatile mode—that is, a balloon 121 of a balloon catheter (not shown) is arranged inside the pump chamber. The balloon 121 is operated in a pulsatile manner in the embodiment of FIG. 14—that is, is filled and emptied intermittently with the auxiliary fluid—and thus serves as a drive for a directional flow of the blood. Second openings 104 are arranged inside the pump chamber section 117. The blood is suctioned into the catheter 101 through the second openings 104, and is directionally transported distally to the first openings 105 in a pulsatile manner in the catheter interior 103 of the line segment 102, according to the drive frequency of the balloon (which can follow an ECG signal, for example), where it then exits the catheter. The distal end of the catheter 101 extends into the pulmonary artery 125. The line segment 102 of the catheter 101 therefore spans (bridges) the entire right heart. The first openings 105 lie, in the embodiment of FIG. 15, in the pulmonary trunk. The line segment 102—that is, both the pump chamber section 117 and the pump tube 106 adjoining the same distally—has a foldable configuration, and thus forms a foldable section 107. A deployable frame 119 is arranged inside the pump chamber 118, which provides sufficient rigidity for the pulsatile operation of the pump chamber 118. For the insertion of the catheter 101 into the body, the line segment 102 is packaged (not shown) in the folded state into an insertion sleeve. The accordingly packaged catheter is advanced via an access in the superior vena cava to the position of the line segment 102, which corresponds to the position shown in FIG. 15, and the line segment 102 penetrates the heart. The insertion sleeve is then withdrawn, whereby the frame 119 is deployed and the line segment 102 unfolds entirely. Due to the configuration of the line segment 102 as a foldable film tube 106, the sensitive heart valves are hardly damaged during the implantation and explantation. A buckling of the film tube 106 in anatomically critical areas within the heart is prevented by the stabilized section 110.

Figure 16:
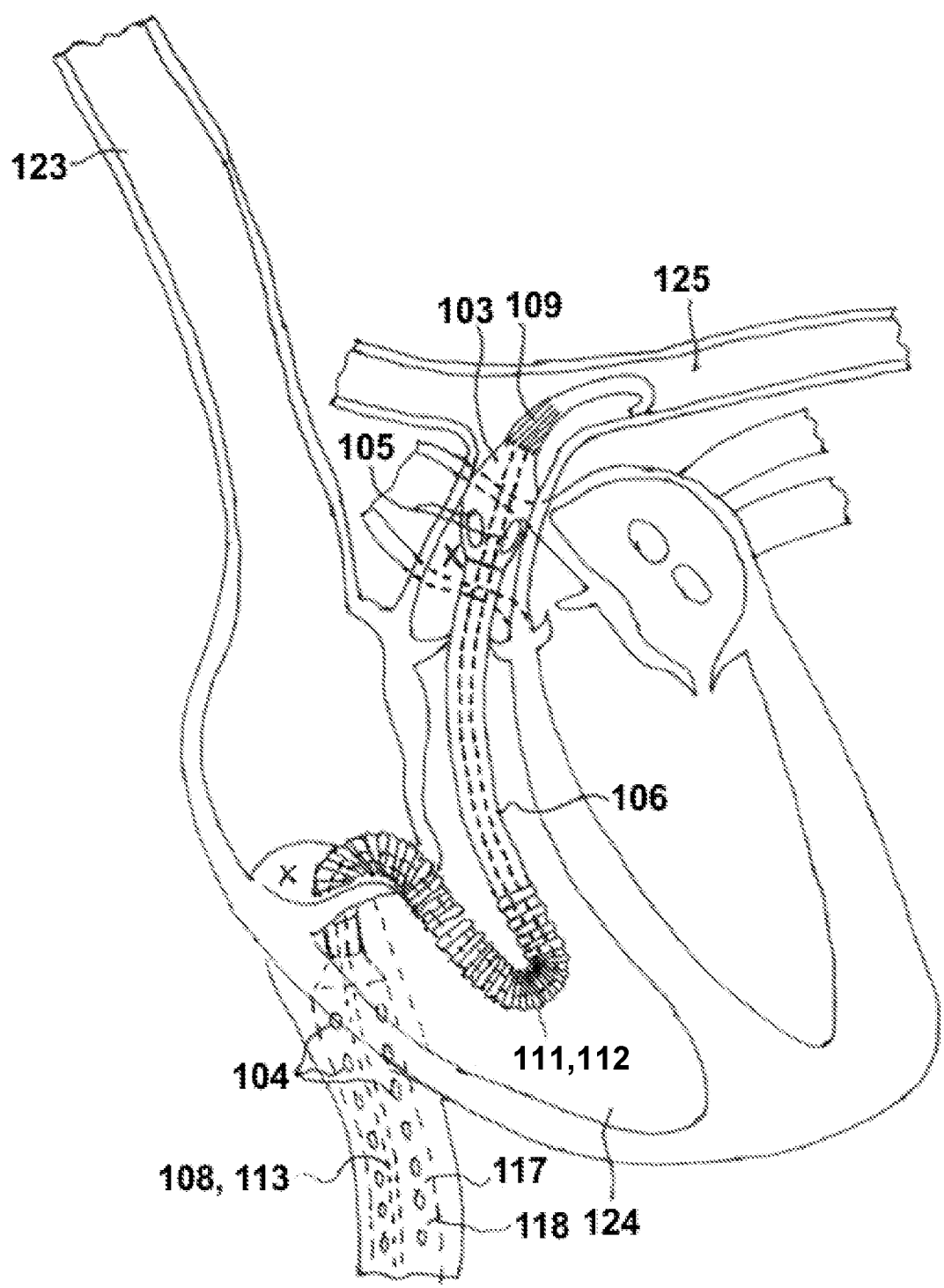

In FIG. 16, the catheter 101, which corresponds structurally to the catheter of FIG. 15, but can have different dimensions in its subsections, is routed via an alternative access of a groin vessel, and is advanced until the pump chamber section 117 is positioned with the second openings 104 in the functional position in the inferior vena cava. The pump tube 106 arranged distally from the pump chamber section spans the right atrium and the right ventricle and therefore extends with its distal end into the pulmonary artery 125. The first openings 105 are arranged in the region of the pulmonary trunk. As already mentioned, this variant routing is standard practice. The catheter, in particular, the length of the line segment 102, the length of the pump chamber section 117, the length of the distal pump tube and/or the position of the stabilized section 110 can be adjusted for optimal fit specifically to this variant routing. For example, the line segment 102 (including the pump chamber section 117) can have a length of 450 mm; the pump chamber section 117 is about 250 mm long, and the distally adjoining pump tube (film tube) 106 is about 200 mm long. The second openings 104 are configured as film valves which are arranged in five radially distributed rows of 20 valves each along the pump chamber section 117.

It is understood that the foregoing description is that of the preferred embodiments of the invention and that various changes and modifications may be made thereto without departing from the spirit and scope of the invention as defined in the appended claims.

LIST OF REFERENCE NUMERALS 1 catheter
2 frame
3 sleeve
4 balloon catheter
5 first opening
6 line
7 third opening
8 auxiliary fluid line
9 second opening
10 check valve
11 valve foil
12 ring
13 aperture
14 balloon
15 spiral
16 additional foil
17 outlet check valve
18 inlet check valve
L line
internal space
S segment
P pump
Q longitudinal axis
X external space
101 catheter
102 line segment
103 internal volume
104 second opening
105 first opening
106 film tube
107 foldable section
108 reinforcement
109 connecting region
110 stabilized section
111 structuring
112 rib-shaped structuring
113 guide tube
114 guidewire
115 tube opening
116 distal section
117 pump chamber section
118 pump chamber
119 frame
120 third opening
121 balloon
122 auxiliary fluid line
123 superior vena cava
124 right ventricle
125 pulmonary artery
126 bulbous expanded section
127 medication port
d distal
p proximal
A rib period (spacing rib to rib)
D1 nominal diameter (rib peak)
D2 core diameter (rib base)
R rib radius
X external

What is claimed is:
1. A catheter for the directional conduction of a pulsating body fluid including blood, the catheter comprising:
 a line segment defining an inner volume and including a distal tube;
 a reinforcement running in said inner volume;
 a pump chamber section arranged proximally as an extension of said line segment;
 said pump chamber section defining a pump chamber having a frame disposed therein;
 a first opening connecting said inner volume to an external volume;

a second opening arranged proximally from said first opening to connect said inner volume to said external volume;

a check valve assigned to said second opening and said check valve including a valve foil having an aperture formed therein offset away from said second opening;

a third opening communicating with said pump chamber;

a balloon being arranged in said pump chamber and within said frame;

said frame having a composition which comprises a shape memory material;

said shape memory material providing sufficient rigidity for a pulsatile operation of said balloon disposed within said frame;

a line for an auxiliary fluid for inflating said balloon being connected to said balloon;

said line passing out through said third opening of the catheter and being connectable to a pump for said auxiliary fluid; and, wherein, during operation of the catheter, said pulsating body fluid is conveyed in the inner volume directionally between the first opening and the second opening by operating said balloon, such that, when deflating, drawing body fluid into the catheter and, when inflating, driving the drawn-in body fluid directionally through said line segment.

2. The catheter according to claim 1, wherein the catheter is configured so as to cause the body fluid to be drawn through said second opening into said inner volume by suction, conducted in said inner volume in a distal direction, and discharged through said first opening out of said inner volume.

3. The catheter according to claim 1, wherein the catheter is configured so as to cause the body fluid to be drawn through said first opening into said inner volume by suction, conducted in said inner volume in a proximal direction, and discharged through said second opening out of said inner volume.

4. The catheter according to claim 1, wherein said check valve is arranged on said line segment.

5. The catheter according to claim 1, wherein said check valve is arranged on said pump chamber.

6. The catheter according to claim 5, wherein a sleeve is arranged on said frame and said check valve is arranged on said sleeve.

7. The catheter according to claim 6, wherein said valve foil is arranged inside said sleeve so as to cause said check valve to act as an inlet valve.

8. The catheter according to claim 6, wherein said valve foil is arranged outside of said sleeve so as to cause said check valve to act as an outlet valve.

9. The catheter according to claim 8, wherein said second opening and said aperture are surrounded by said attachment line.

10. The catheter according to claim 8, wherein said sleeve has a lower elasticity than said valve foil.

11. The catheter according to claim 6, wherein said sleeve and said valve foil conjointly define an interface between said second opening and said aperture; and, said valve foil being at least partially attached to said sleeve so as to be displaceable between a first position whereat said valve foil covers said second opening to prevent passage of the body fluid through said second opening and a second position whereat the body fluid can flow through said second opening along said interface and through said aperture.

12. The catheter according to claim 6, wherein said sleeve and said valve foil conjointly define an interface between said second opening and said aperture; and, said valve foil being attached to said sleeve along a line enclosing said second opening and said aperture within a region so as to permit said valve foil to be displaceable between a first position whereat said valve foil covers said second opening to prevent passage of the body fluid through said second opening and a second position whereat a chamber is formed within said region enclosed by said sleeve and said valve foil so as to facilitate the flow of the body fluid through said second opening through said chamber along said interface and through said aperture.

13. The catheter according to claim 6, wherein said valve foil is connected to said sleeve along an attachment line.

14. The catheter of claim 1, wherein said aperture has an area between 5 mm$^2$ and 500 mm$^2$.

15. The catheter of claim 1 further comprising:
a plurality of said second openings;
a plurality of said check valves assigned to corresponding ones of said second openings; and,
a plurality of said valve foils assigned to corresponding ones of said check valves.

16. The catheter of claim 1, wherein said check valve includes a group of several of said second openings; and, each second opening of the group of second openings is entirely covered by said valve foil when in said first position.

17. The catheter of claim 1, wherein said distal tube comprises a material that comprises a polyurethane.

18. The catheter of claim 1, wherein the reinforcement includes a guide tube defining a guide tube interior; and, said guide tube has an outer diameter lying in a range between 0.5 mm and 2 mm.

19. The catheter according to claim 18, wherein said guide tube has a distal end and a medication port at said distal end.

20. The catheter according to claim 18, wherein said guide tube is configured to be pushed over a guide wire for determinatively positioning the catheter.

21. The catheter according to claim 20, wherein said guide tube has a distal end and a medication port at said distal end.

22. The catheter of claim 1, wherein said distal tube comprises a plurality of second ports which are at least partially arranged at a distance from the distal end of a film tube.

23. The catheter according to claim 1, wherein said shape memory material is one of the following: nitinol, a shape memory polymer, or a shape memory ceramic.

24. The catheter according to claim 1, wherein said frame is switchable between a first configuration with a first size of the inner volume and a second configuration with a second size of the inner volume bigger than the first size.

* * * * *